United States Patent
Kane et al.

(10) Patent No.: US 10,617,874 B2
(45) Date of Patent: *Apr. 14, 2020

(54) SYSTEMS AND METHODS FOR ACTIVITY LEVEL PACING

(71) Applicant: CARDIAC PACEMAKERS, INC., St. Paul, MN (US)

(72) Inventors: Michael J. Kane, St. Paul, MN (US); Paul Huelskamp, St. Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 270 days.

This patent is subject to a terminal disclaimer.

(21) Appl. No.: 15/797,797

(22) Filed: Oct. 30, 2017

(65) Prior Publication Data

US 2018/0117338 A1 May 3, 2018

Related U.S. Application Data

(60) Provisional application No. 62/424,876, filed on Nov. 21, 2016, provisional application No. 62/415,132, filed on Oct. 31, 2016.

(51) Int. Cl.
*A61N 1/365* (2006.01)
*A61N 1/375* (2006.01)
(Continued)

(52) U.S. Cl.
CPC ........ *A61N 1/36542* (2013.01); *A61B 5/1116* (2013.01); *A61B 5/1118* (2013.01); (Continued)

(58) Field of Classification Search
CPC .............................................. A61N 1/36542
See application file for complete search history.

(56) References Cited

U.S. PATENT DOCUMENTS 3,835,864 A 9/1974 Rasor et al.
3,943,936 A 3/1976 Rasor et al.
(Continued)

FOREIGN PATENT DOCUMENTS

AU 2008279789 B2 10/2011
AU 2008329620 B2 5/2014
(Continued)

OTHER PUBLICATIONS

US 8,886,318 B2, 11/2014, Jacobson et al. (withdrawn)
(Continued)

*Primary Examiner* — Alyssa M Alter
(74) *Attorney, Agent, or Firm* — Seager, Tufte & Wickhem LLP

(57) ABSTRACT

Systems, devices, and methods for pacing a heart of a patient are disclosed. An illustrative method may include determining a motion level of the patient using a motion sensor of an implantable medical device secured relative to a patient's heart, and setting a pacing rate based at least in part on the patient's motion level. The patient's motion level may be determined by, for example, comparing the motion level sensed by the motion sensor during a current heart beat to a motion level associated with one or more previous heart beats. Noise may occur in the motion level measurements during those heart beats that transition between an intrinsically initiated heart beat and pace initiated heart beat. Various techniques may be applied to the motion level measurements to help reduce the effect of such noise.

20 Claims, 13 Drawing Sheets

(51) Int. Cl.
  *A61B 5/11* (2006.01)
  *A61B 5/00* (2006.01)
  *A61N 1/372* (2006.01)

(52) U.S. Cl.
  CPC ............ *A61B 5/686* (2013.01); *A61B 5/7217* (2013.01); *A61N 1/36535* (2013.01); *A61N 1/3756* (2013.01); *A61N 1/37288* (2013.01); *A61N 1/37512* (2017.08); *A61B 2560/0223* (2013.01); *A61B 2562/0219* (2013.01)

(56) References Cited

U.S. PATENT DOCUMENTS

| | | | |
|---|---|---|---|
| 4,142,530 A | 3/1979 | Wittkampf | |
| 4,151,513 A | 4/1979 | Menken et al. | |
| 4,157,720 A | 6/1979 | Greatbatch | |
| RE30,366 E | 8/1980 | Rasor et al. | |
| 4,243,045 A | 1/1981 | Maas | |
| 4,250,884 A | 2/1981 | Hartlaub et al. | |
| 4,256,115 A | 3/1981 | Bilitch | |
| 4,263,919 A | 4/1981 | Levin | |
| 4,310,000 A | 1/1982 | Lindemans | |
| 4,312,354 A | 1/1982 | Walters | |
| 4,323,081 A | 4/1982 | Wiebusch | |
| 4,357,946 A | 11/1982 | Dutcher et al. | |
| 4,365,639 A | 12/1982 | Goldreyer | |
| 4,440,173 A | 4/1984 | Hudziak et al. | |
| 4,476,868 A | 10/1984 | Thompson | |
| 4,522,208 A | 6/1985 | Buffet | |
| 4,537,200 A | 8/1985 | Widrow | |
| 4,556,063 A | 12/1985 | Thompson et al. | |
| 4,562,841 A | 1/1986 | Brockway et al. | |
| 4,593,702 A | 6/1986 | Kepski et al. | |
| 4,593,955 A | 6/1986 | Leiber | |
| 4,630,611 A | 12/1986 | King | |
| 4,635,639 A | 1/1987 | Hakala et al. | |
| 4,674,508 A | 6/1987 | DeCote | |
| 4,712,554 A | 12/1987 | Garson | |
| 4,729,376 A | 3/1988 | DeCote | |
| 4,754,753 A | 7/1988 | King | |
| 4,759,366 A | 7/1988 | Callaghan | |
| 4,776,338 A | 10/1988 | Lekholm et al. | |
| 4,787,389 A | 11/1988 | Tarjan | |
| 4,793,353 A | 12/1988 | Borkan | |
| 4,819,662 A | 4/1989 | Heil et al. | |
| 4,858,610 A | 8/1989 | Callaghan et al. | |
| 4,886,064 A | 12/1989 | Strandberg | |
| 4,887,609 A | 12/1989 | Cole | |
| 4,928,688 A | 5/1990 | Mower | |
| 4,967,746 A | 11/1990 | Vandegriff | |
| 4,987,897 A | 1/1991 | Funke | |
| 4,989,602 A | 2/1991 | Sholder et al. | |
| 5,012,806 A | 5/1991 | De Bellis | |
| 5,036,849 A | 8/1991 | Hauck et al. | |
| 5,040,534 A | 8/1991 | Mann et al. | |
| 5,058,581 A | 10/1991 | Silvian | |
| 5,078,134 A | 1/1992 | Heilman et al. | |
| 5,109,845 A | 5/1992 | Yuuchi et al. | |
| 5,113,859 A | 5/1992 | Funke | |
| 5,113,869 A | 5/1992 | Nappholz et al. | |
| 5,117,824 A | 6/1992 | Keimel et al. | |
| 5,127,401 A | 7/1992 | Grevious et al. | |
| 5,133,353 A | 7/1992 | Hauser | |
| 5,144,950 A | 9/1992 | Stoop et al. | |
| 5,170,784 A | 12/1992 | Ramon et al. | |
| 5,179,945 A | 1/1993 | Van Hofwegen et al. | |
| 5,193,539 A | 3/1993 | Schulman et al. | |
| 5,193,540 A | 3/1993 | Schulman et al. | |
| 5,241,961 A | 9/1993 | Henry | |
| 5,243,977 A | 9/1993 | Trabucco et al. | |
| 5,259,387 A | 11/1993 | DePinto | |
| 5,269,326 A | 12/1993 | Verrier | |
| 5,284,136 A | 2/1994 | Hauck et al. | |
| 5,300,107 A | 4/1994 | Stokes et al. | |
| 5,301,677 A | 4/1994 | Hsung | |
| 5,305,760 A | 4/1994 | McKown et al. | |
| 5,312,439 A | 5/1994 | Loeb | |
| 5,313,953 A | 5/1994 | Yomtov et al. | |
| 5,314,459 A | 5/1994 | Swanson et al. | |
| 5,318,597 A | 6/1994 | Hauck et al. | |
| 5,324,316 A | 6/1994 | Schulman et al. | |
| 5,331,966 A | 7/1994 | Bennett et al. | |
| 5,334,222 A | 8/1994 | Salo et al. | |
| 5,342,408 A | 8/1994 | deCoriolis et al. | |
| 5,350,409 A | 9/1994 | Stoop et al. | |
| 5,370,667 A | 12/1994 | Alt | |
| 5,372,606 A | 12/1994 | Lang et al. | |
| 5,376,106 A | 12/1994 | Stahmann et al. | |
| 5,383,915 A | 1/1995 | Adams | |
| 5,388,578 A | 2/1995 | Yomtov et al. | |
| 5,404,877 A | 4/1995 | Nolan et al. | |
| 5,405,367 A | 4/1995 | Schulman et al. | |
| 5,411,031 A | 5/1995 | Yomtov | |
| 5,411,525 A | 5/1995 | Swanson et al. | |
| 5,411,535 A | 5/1995 | Fujii et al. | |
| 5,413,592 A | 5/1995 | Schroeppel | |
| 5,456,691 A | 10/1995 | Snell | |
| 5,458,622 A | 10/1995 | Alt | |
| 5,466,246 A | 11/1995 | Silvian | |
| 5,468,254 A | 11/1995 | Hahn et al. | |
| 5,472,453 A | 12/1995 | Alt | |
| 5,522,866 A | 6/1996 | Fernald | |
| 5,540,727 A | 7/1996 | Tockman et al. | |
| 5,545,186 A | 8/1996 | Olson et al. | |
| 5,545,202 A | 8/1996 | Dahl et al. | |
| 5,571,146 A | 11/1996 | Jones et al. | |
| 5,591,214 A | 1/1997 | Lu | |
| 5,593,431 A | 1/1997 | Sheldon | |
| 5,620,466 A | 4/1997 | Haefner et al. | |
| 5,634,938 A | 6/1997 | Swanson et al. | |
| 5,649,968 A | 7/1997 | Alt et al. | |
| 5,662,688 A | 9/1997 | Haefner et al. | |
| 5,674,259 A | 10/1997 | Gray | |
| 5,683,426 A | 11/1997 | Greenhut et al. | |
| 5,683,432 A | 11/1997 | Goedeke et al. | |
| 5,706,823 A | 1/1998 | Wodlinger | |
| 5,709,215 A | 1/1998 | Perttu et al. | |
| 5,720,770 A | 2/1998 | Nappholz et al. | |
| 5,728,154 A | 3/1998 | Crossett et al. | |
| 5,741,314 A | 4/1998 | Daly et al. | |
| 5,741,315 A | 4/1998 | Lee et al. | |
| 5,752,976 A | 5/1998 | Duffin et al. | |
| 5,752,977 A | 5/1998 | Grevious et al. | |
| 5,755,736 A | 5/1998 | Gillberg et al. | |
| 5,759,199 A | 6/1998 | Snell et al. | |
| 5,774,501 A | 6/1998 | Halpern et al. | |
| 5,792,195 A | 8/1998 | Carlson et al. | |
| 5,792,202 A | 8/1998 | Rueter | |
| 5,792,203 A | 8/1998 | Schroeppel | |
| 5,792,205 A | 8/1998 | Alt et al. | |
| 5,792,208 A | 8/1998 | Gray | |
| 5,814,089 A | 9/1998 | Stokes et al. | |
| 5,827,216 A | 10/1998 | Igo et al. | |
| 5,836,985 A | 11/1998 | Rostami et al. | |
| 5,836,987 A | 11/1998 | Baumann et al. | |
| 5,842,977 A | 12/1998 | Lesho et al. | |
| 5,855,593 A | 1/1999 | Olson et al. | |
| 5,873,894 A | 2/1999 | Vandegriff et al. | |
| 5,891,184 A | 4/1999 | Lee et al. | |
| 5,897,586 A | 4/1999 | Molina | |
| 5,899,876 A | 5/1999 | Flower | |
| 5,899,928 A | 5/1999 | Sholder et al. | |
| 5,919,214 A | 7/1999 | Ciciarelli et al. | |
| 5,935,078 A | 8/1999 | Feierbach | |
| 5,941,906 A | 8/1999 | Barreras, Sr. et al. | |
| 5,944,744 A | 8/1999 | Paul et al. | |
| 5,954,757 A | 9/1999 | Gray | |
| 5,978,713 A | 11/1999 | Prutchi et al. | |
| 5,991,660 A | 11/1999 | Goyal | |
| 5,991,661 A | 11/1999 | Park et al. | |
| 5,999,848 A | 12/1999 | Gord et al. | |
| 5,999,857 A | 12/1999 | Weijand et al. | |
| 6,016,445 A | 1/2000 | Baura | |
| 6,026,320 A | 2/2000 | Carlson et al. | |

(56) References Cited

U.S. PATENT DOCUMENTS

| | | |
|---|---|---|
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B2 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |

(56) References Cited

U.S. PATENT DOCUMENTS

| | | |
|---|---|---|
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |

(56) References Cited

U.S. PATENT DOCUMENTS

| | | |
|---|---|---|
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bomzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bomzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bomzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |

(56) References Cited

U.S. PATENT DOCUMENTS

| | | |
|---|---|---|
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bomzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,080,887 B2 | 9/2018 | Schmidt et al. |
| 10,080,888 B2 | 9/2018 | Kelly et al. |
| 10,080,900 B2 | 9/2018 | Ghosh et al. |
| 10,080,903 B2 | 9/2018 | Willis et al. |
| 10,086,206 B2 | 10/2018 | Sambelashvili |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |

(56) References Cited

U.S. PATENT DOCUMENTS

| | | |
|---|---|---|
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0142864 A1 | 6/2007 | Libbus et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0004664 A1 | 1/2008 | Hopper et al. |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |

(56) References Cited

U.S. PATENT DOCUMENTS

| | | |
|---|---|---|
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |

(56) References Cited

U.S. PATENT DOCUMENTS

| | | |
|---|---|---|
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2015/0360036 A1 | 12/2015 | Kane et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0250480 A1 | 9/2016 | Sheldon et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2018/0117339 A1* | 5/2018 | Huelskamp ......... A61N 1/37512 |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2471452 A1 | 7/2012 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2005000206 A3 | 1/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |

(56) References Cited

FOREIGN PATENT DOCUMENTS

| WO | 2013184787 A1 | 12/2013 |
| WO | 2014120769 A1 | 8/2014 |

OTHER PUBLICATIONS

International Search Report and Written Opinion for Application No. PCT/US2017/059048, 32 pages, dated Feb. 8, 2018.
"Instructions for Use System 1, Leadless Cardiac Pacemaker (LCP) and Delivery Catheter," Nanostim Leadless Pacemakers, pp. 1-28, 2013.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Seyedi et al., "A Survey on Intrabody Communications for Body Area Network Application," IEEE Transactions on Biomedical Engineering, vol. 60(8): 2067-2079, 2013.
Spickler et al., "Totally Self-Contained Intracardiac Pacemaker," Journal of Electrocardiology, vol. 3(3&4): 324-331, 1970.
Wegmüller, "Intra-Body Communication for Biomedical Sensor Networks," Diss. ETH, No. 17323, 1-173, 2007.

\* cited by examiner

SYSTEMS AND METHODS FOR ACTIVITY LEVEL PACING

CROSS REFERENCE TO RELATED APPLICATIONS

This application claims the benefit of U.S. Provisional Patent Application Ser. No. 62/424,876 filed on Nov. 21, 2016, and U.S. Provisional Patent Application Ser. No. 62/415,132 filed on Oct. 31, 2016, the disclosures of which are incorporated herein by reference.

The present disclosure generally relates to systems, devices, and methods for delivering pacing therapy to a patient, and more particularly, to systems, devices, and methods for modulating pacing therapy based on an activity level of the patient.

BACKGROUND

Pacing instruments can be used to treat patients suffering from various heart conditions that result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, such devices may modulate delivered pacing therapy based on a patient's activity level, which is sometime referred to as rate responsive pacing.

SUMMARY

The present disclosure generally relates to systems, devices, and methods for delivering pacing therapy to a patient, and more particularly, to systems, devices, and methods for modulating pacing therapy based on an activity level of the patient.

In an illustrative embodiment, an implantable medical device (IMD) implantable within a patient's may comprise two or more sensors including a motion sensor and a controller operatively coupled to the two or more sensors. The controller may identify a plurality of heart beats using one or more of the sensors, each of the plurality of heart beats having a systole phase and diastole phase. The controller may identify each of two or more of the plurality of heart beats as an intrinsically initiated heart beat or a pace initiated heart beat, and identify a calibration time window. During the calibration time window, the controller may identify a baseline intrinsic motion level by identifying a motion level of the IMD using the motion sensor during the systole phase of N intrinsically initiated heart beats, where N is greater than two and identify a baseline pace motion level by identifying a motion level of the IMD using the motion sensor during the systole phase of N pace initiated heart beats, where N is greater than two. The controller may then determine an offset based at least in part on the baseline intrinsic motion level and the baseline pace motion level. After the calibration time window and for an intrinsically initiated heart beat that immediately follows a pace initiated heart beat, the controller may identify a motion level of the IMD using the motion sensor during the systole phase of the intrinsically initiated heart beat and apply the offset, and compare the identified motion level of the IMD with the applied offset to a motion level of the IMD identified for the immediately preceding pace initiated heart beat, and identify a motion level of the patient based at least in part on the comparison. Based at least in part on the identified motion level of the patient, the controller may set a pacing rate parameter.

Additionally, or alternatively to the first illustrative embodiment, after the calibration time window and for a pace initiated heart beat that immediately follows an intrinsic initiated heart beat, the controller may identify a motion level of the IMD using the motion sensor during the systole phase of the pace initiated heart beat and apply the offset, and compare the identified motion level of the LMD with the applied offset to a motion level of the LMD identified for the immediately preceding intrinsically initiated heart beat, and identify a motion level of the patient based at least in part on the comparison.

Additionally, or alternatively, in any of the above embodiments with respect to the first illustrative embodiment, after the calibration time window and for an intrinsically initiated heart beat that immediately follows an intrinsically initiated heart beat, the controller may identify a motion level of the IMD using the motion sensor during the systole phase of the intrinsically initiated heart beat, and compare the identified motion level of the IMD to a motion level of the IMD identified for one or more previous intrinsically initiated heart beats, and identify a motion level of the patient based at least in part on the comparison.

Additionally, or alternatively, in any of the above embodiments with respect to the first illustrative embodiment, after the calibration time window and for a pace initiated heart beat that immediately follows a pace initiated heart beat, the controller may identify a motion level of the IMD using the motion sensor during the systole phase of the pace initiated heart beat, and compare the identified motion level of the IMD to a motion level of the IMD identified for one or more previous pace initiated heart beats, and identify the motion level of the patient based at least in part on the comparison.

Additionally, or alternatively, in any of the above embodiments with respect to the first illustrative embodiment, the N intrinsically initiated heart beats may be N consecutive intrinsically initiated heart beats.

Additionally, or alternatively, in any of the above embodiments with respect to the first illustrative embodiment, the N pace initiated heart beats may be N consecutive pace initiated heart beats.

Additionally, or alternatively, in any of the above embodiments with respect to the first illustrative embodiment, the calibration time window may be a time window where patient activity is expected to be low.

Additionally, or alternatively, in any of the above embodiments with respect to the first illustrative embodiment, the calibration time window may be initiated after a particular posture of the patient is detected by the IMD.

Additionally, or alternatively, in any of the above embodiments with respect to the first illustrative embodiment, the IMD may detect each of N different postures, wherein N is greater than two, and the controller may identify a calibration time window for each N different postures. During each calibration time window, the controller may identify a baseline intrinsic motion level for the corresponding posture by identifying a motion level of the IMD using the motion sensor during the systole phase of N intrinsically initiated heart beats, where N is greater than two. The controller may also identify a baseline pace motion level for the corresponding posture by identifying a motion level of the IMD using the motion sensor during the systole phase of N pace initiated heart beats, where N is greater than two. Based at least in part on the baseline intrinsic motion level that corresponds to the corresponding posture and the baseline pace motion level that corresponds to the corresponding posture, the controller may determine an offset for each of the N different postures. After the calibration time window for each of the N different postures, the controller may identify a current posture of the patient as one of the N different postures. For an intrinsically initiated heart beat that immediately follows a pace initiated heart beat, the controller may identify a motion level of the IMD using the motion sensor during the systole phase of the intrinsically initiated heart beat, apply the offset that corresponds to the current posture, compare the identified motion level of the with the applied offset that corresponds to the current posture to a motion level of the IMD identified for the immediately preceding pace initiated heart beat, and identify a motion level of the patient based at least in part on the comparison. For a pace initiated heart beat that immediately follows an intrinsically initiated heart beat, the controller may identify a motion level of the IMD using the motion sensor during the systole phase of the pace initiated heart beat, apply the offset that corresponds to the current posture, compare the identified motion level of the IMD with the applied offset that corresponds to the current posture to a motion level of the IMD identified for the immediately preceding intrinsically initiated heart beat, and identify a motion level of the patient based at least in part on the comparison.

Additionally, or alternatively, in any of the above embodiments with respect to the first illustrative embodiment, wherein the calibration time window is initiated at a particular time of day.

Additionally, or alternatively, in any of the above embodiments with respect to the first illustrative embodiment, wherein the calibration time window is initiated after the motion level of the patient falls below a threshold for at least a predetermined length of time.

Additionally, or alternatively, in any of the above embodiments with respect to the first illustrative embodiment, wherein during the calibration time window the controller may pace the patient's heart at a pacing rate that is above a current intrinsic heart rate of the patient, and while pacing the patient's heart at the pacing rate that is above the current intrinsic heart rate of the patient, identify the baseline pace motion level by identifying the motion level of the using the motion sensor during the systole phase of N pace initiated heart beats, where N is greater than two.

In another illustrative embodiment, a method for identifying an activity level of a patient using a motion sensor implanted within the patient's heart may comprise identifying a plurality of heart beats using one or more of the sensors, each of the plurality of heart beats having a systole phase and diastole phase, identifying each of two or more of the plurality of heart beats as an intrinsically initiated heart beat or a pace initiated heart beat, and identifying a calibration time window. During the calibration time window, the method may comprise identifying a baseline intrinsic motion level by identifying a motion level of the IMD using the motion sensor during the systole phase of N intrinsically initiated heart beats, where N is greater than two, and identifying a baseline pace motion level by identifying a motion level of the IMD using the motion sensor during the systole phase of N pace initiated heart beats, where N is greater than two. The method may further comprise determining an offset based at least in part on the baseline intrinsic motion level and the baseline pace motion level. After the calibration time window and for an intrinsically initiated heart beat that immediately follows a pace initiated heart beat, the may comprise identifying a motion level of the IMD using the motion sensor during the systole phase of the intrinsically initiated heart beat and apply the offset, comparing the identified motion level of the IMD with the applied offset to a motion level of the IMD identified for the immediately preceding pace initiated heart beat, and identifying a motion level of the patient based at least in part on the comparison.

Additionally, or alternatively, the second illustrative embodiment may further comprise, setting a pacing rate parameter based at least in part on the identified motion level of the patient.

Additionally, or alternatively, to any of the above embodiments with respect to the second illustrative embodiment, after the calibration time window and for a pace initiated heart beat that immediately follows an intrinsic initiated heart beat, the method may further comprise identifying a motion level of the IMD using the motion sensor during the systole phase of the pace initiated heart beat and apply the offset, comparing the identified motion level of the IMD with the applied offset to a motion level of the IMD identified for the immediately preceding intrinsically initiated heart beat, and identifying a motion level of the patient based at least in part on the comparison.

Additionally, or alternatively, to any of the above embodiments with respect to the second illustrative embodiment, after the calibration time window and for an intrinsically initiated heart beat that immediately follows an intrinsically initiated heart beat, the method may further comprise identifying a motion level of the IMD using the motion sensor during the systole phase of the intrinsically initiated heart beat, comparing the identified motion level of the IMD to a motion level of the identified for one or more previous intrinsically initiated heart beats, and identifying a motion level of the patient based at least in part on the comparison. After the calibration time window and for a pace initiated heart beat that immediately follows a pace initiated heart beat, the method may further comprise identifying a motion level of the IMD using the motion sensor during the systole phase of the pace initiated heart beat, comparing the identified motion level of the IMD to a motion level of the IMD identified for one or more previous pace initiated heart beats, and identifying the motion level of the patient based at least in part on the comparison.

Additionally, or alternatively, to any of the above embodiments with respect to the second illustrative embodiment, the N intrinsically initiated heart beats may be N consecutive intrinsically initiated heart beats, and the N pace initiated heart beats may be N consecutive pace initiated heart beats.

In another illustrative embodiment, a leadless cardiac pacemaker (LCP) implantable within a patient's heart may comprise a housing, two or more electrodes secured relative to the housing, an accelerometer situated inside of the housing, and circuitry situated inside of the housing and operatively coupled to the two or more electrodes and the accelerometer. The two or more electrodes are configured to sense electrical signals of the patient's heart. The circuitry may identify a plurality of heart beats using two or more of the electrodes, each of the plurality of heart beats having a systole phase and diastole phase. The circuitry may also identify each of two or more of the plurality of heart beats as an intrinsically initiated heart beat or a pace initiated heart beat, and identify a calibration time window. During the calibration time window, the circuitry may identify a baseline intrinsic motion level by identifying a motion level of the LCP using the accelerometer during the systole phase of N intrinsically initiated heart beats, where N is greater than two, and identify a baseline pace motion level by identifying a motion level of the LCP using the accelerometer during the systole phase of N pace initiated heart beats, where N is greater than two. Based at least in part on the baseline intrinsic motion level and the baseline pace motion level, the circuitry may identify an offset. After the calibration time window and for an intrinsically initiated heart beat that immediately follows a pace initiated heart beat, the circuitry may identify a motion level of the LCP using the accelerometer during the systole phase of the intrinsically initiated heart beat and apply the offset, compare the identified motion level of the LCP with the applied offset to a motion level of the LCP identified for the immediately preceding pace initiated heart beat, and identify a motion level of the patient based at least in part on the comparison. After the calibration time window and for a pace initiated heart beat that immediately follows an intrinsic initiated heart beat, the circuitry may identify a motion level of the LCP using the accelerometer during the systole phase of the pace initiated heart beat and apply the offset, compare the identified motion level of the LCP with the applied offset to a motion level of the LCP identified for the immediately preceding intrinsically initiated heart beat, and identify a motion level of the patient based at least in part on the comparison. After the calibration time window and for an intrinsically initiated heart beat that immediately follows an intrinsically initiated heart beat, the circuitry may identify a motion level of the LCP using the accelerometer during the systole phase of the intrinsically initiated heart beat, compare the identified motion level of the LCP to a motion level of the LCP identified for one or more previous intrinsically initiated heart beats, and identify a motion level of the patient based at least in part on the comparison. After the calibration time window and for a pace initiated heart beat that immediately follows a pace initiated heart beat, the circuitry may identify a motion level of the LCP using the accelerometer during the systole phase of the pace initiated heart beat, and compare the identified motion level of the LCP to a motion level of the LCP identified for one or more previous pace initiated heart beats, and identify the motion level of the patient based at least in part on the comparison. Based at least in part on the identified motion level of the patient, the circuitry may set a pacing rate parameter.

Additionally, or alternatively, to the third illustrative embodiment, the N intrinsically initiated heart beats may be N consecutive intrinsically initiated heart beats, and the N pace initiated heart beats may be N consecutive pace initiated heart beats.

Additionally, or alternatively, to any of the above embodiments with respect to the third illustrative embodiment, the calibration time window may be a time window where patient activity is expected to be low.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
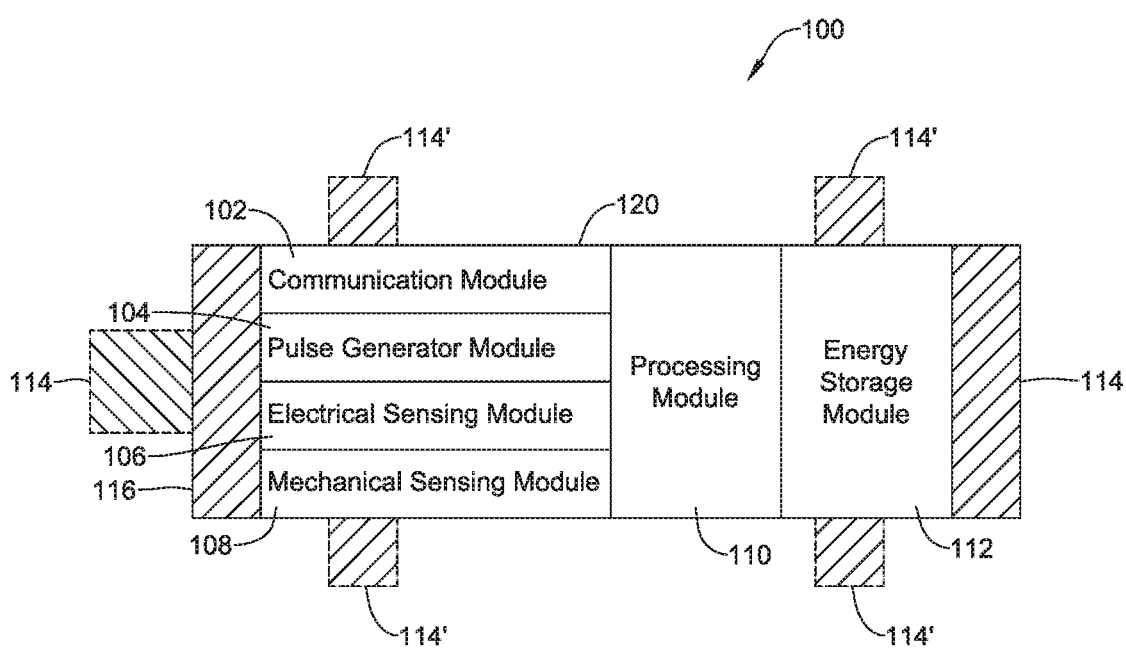
FIG. 1 is a schematic block diagram of an illustrative leadless cardiac pacemaker (LCP) according to one embodiment of the present disclosure.

While the disclosure is amenable to various modifications and alternative forms, specifics thereof have been shown by way of embodiment in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

This disclosure describes systems, devices, and methods for modifying delivery of pacing pulses according to a motion level of a patient. For example, devices of the present disclosure may be configured to determine a motion level of a patient. The devices may then adjust the rate of delivery of pacing pulses in accordance with the determined motion level. As one example, the devices may slow the delivery rate of pacing pulses during periods of lower patient motion relative to a delivery rate of pacing pulses during periods of higher patient motion.

FIG. 1 is a conceptual schematic block diagram of an implantable medical device (IMD), such as an illustrative leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. The disclosed concepts may be implemented in other IMDs and/or other devices including, but not limited to, pacemakers with leads, defibrillators, and/or other implantable or non-implantable devices.

As can be seen in FIG. 1, LCP 100 may be a compact device with all components housed within LCP 100 or directly on housing 120. In some instances, LCP 100 may include communication module 102, pulse generator module 104, electrical sensing module 106 (e.g., including one or more electrical sensors), mechanical sensing module 108 (e.g., including one or more mechanical sensors), processing module 110 (e.g., a controller including memory and one or more processors), energy storage module 112, and electrodes 114, 114'. Via circuitry, the electrodes 114, 114' may be part of and/or may be in communication with (e.g., operatively coupled to) the communication module 102, the pulse generator module 104, electrical sensing module 106, the mechanical sensing module 108, the processing module 110, and/or the energy storage module 112.

As depicted in FIG. 1, LCP 100 may include electrodes 114, which can be secured relative to housing 120 and electrically exposed to tissue and/or blood surrounding LCP 100. Electrodes 114 may generally conduct electrical signals to and/or from LCP 100 and the surrounding tissue and/or blood. Such electrical signals may include communication signals, electrical stimulation pulses, and intrinsic cardiac electrical signals, to name a few. Intrinsic cardiac electrical signals may include electrical signals generated by the heart and may be represented by an electrocardiogram (ECG). The electrodes may be considered a sensor capable of sensing each of a plurality of heart beats.

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 (e.g., two or more electrodes 114) are secured directly to housing 120, an insulative material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120.

As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120, in some instances, at least some of electrodes 114 and/or 114' may be spaced from one another by a distance of twenty, thirty, forty, fifty millimeters), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology.

Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, LCP 100 may vary the rate at which pulse generator module 104 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 104 may generate electrical stimulation pulses suitable for neurostimulation therapy or the like.

Pulse generator module 104 may include one or more capacitor elements and/or other charge storage devices to aid in generating and delivering appropriate electrical stimulation pulses. In at least some embodiments, pulse generator module 104 may use energy stored in energy storage module 112 to generate the electrical stimulation pulses. In some particular embodiments, pulse generator module 104 may include a switching circuit that is connected to energy storage module 112 and may connect energy storage module 112 to one or more of electrodes 114/114' to generate electrical stimulation pulses.

LCP 100 may include an electrical sensing module 106. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. The electrical sensing module 106 may, in some cases, be configured to identify each of a plurality of heart beats as an intrinsically initiated heart beat or a pace initiated heart beat.

Further, LCP 100 may include a mechanical sensing module 108. Mechanical sensing module 108 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters.

Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the 100.

Processing module 110 may be configured to direct the operation of LCP 100 and may, in some embodiments, be termed a controller. For example, processing module 110 may be configured to receive cardiac electrical signals from electrical sensing module 106 and/or physiological signals from mechanical sensing module 108. Based on the received signals, processing module 110 may, for example, adjust the rate of pacing based on the activity level of the patient (e.g, rate adaptive pacing). When so provided, processing module 110 may monitor one or more physiological parameters of the patient which may indicate a need for an increased heart rate (e.g. due to increased metabolic demand) and increase the rate at which pulse generator module 104 generates electrical stimulation pulses. Determining an activity level of the patient using a motion sensor (e.g. accelerometer) of the mechanical sensing module 108 of the LCP 100 can be challenging because the motion detected by the motion sensor not only includes the activity level of the patient but also the motion of the beating heart. FIGS. 6-10 describes illustrative methods for aiding in rate responsive pacing using a motion sensor accelerometer) in an LCP.

In some cases, the processing module 110 may determine occurrences and types of arrhythmias and other determinations such as whether LCP 100 has become dislodged. Processing module 110 may further receive information from communication module 102. In some embodiments, processing module 110 may additionally use such received information to determine occurrences and types of arrhythmias and/or and other determinations such as whether LCP 100 has become dislodged. In still some additional embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining an occurrence of an arrhythmia, processing module 110 may control pulse generator module 104 to generate electrical stimulation pulses in accordance with one or more electrical stimulation therapies to treat the determined arrhythmia. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold.

For ATP therapy, processing module 110 may control pulse generator module 104 to deliver pacing pulses at a rate faster than an intrinsic heart rate of a patient in an attempt to force the heart to beat in response to the delivered pacing pulses rather than in response to intrinsic cardiac electrical signals. Once the heart is following the pacing pulses, processing module 110 may control pulse generator module 104 to reduce the rate of delivered pacing pulses down to a safer level. In Cardiac Resynchronization Therapy (CRT), processing module 110 may control pulse generator module 104 to deliver pacing pulses in coordination with another device to cause the heart to contract more efficiently. In cases where pulse generator module 104 is capable of generating defibrillation and/or cardioversion pulses for defibrillation/cardioversion therapy, processing module 110 may control pulse generator module 104 to generate such defibrillation and/or cardioversion pulses. In some cases, processing module 110 may control pulse generator module 104 to generate electrical stimulation pulses to provide electrical stimulation therapies different than those examples described above.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may help LCP 100 provide more effective delivery of electrical stimulation therapy.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In further embodiments, processing module 110 may control switching circuitry by which communication module 102 and pulse generator module 104 deliver communication signals and/or electrical stimulation pulses to tissue of the patient. As described above, both communication module 102 and pulse generator module 104 may include circuitry for connecting one or more electrodes 114 and/114' to communication module 102 and/or pulse generator module 104 so those modules may deliver the communication signals and electrical stimulation pulses to tissue of the patient. The specific combination of one or more electrodes by which communication module 102 and/or pulse generator module 104 deliver communication signals and electrical stimulation pulses may influence the reception of communication signals and/or the effectiveness of electrical stimulation pulses. Although it was described that each of communication module 102 and pulse generator module 104 may include switching circuitry, in some embodiments, LCP 100 may have a single switching module connected to the communication module 102, the pulse generator module 104, and electrodes 114 and/or 114'. In such embodiments, processing module 110 may control the switching module to connect modules 102/104 and electrodes 114/114' as appropriate.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip. In still other embodiments, processing module 110 may not be a single component. For example, processing module 110 may include multiple components positioned at disparate locations within LCP 100 in order to perform the various described functions. For example, certain functions may be performed in one component of processing module 110, while other functions are performed in a separate component of processing module 110, Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. In still other embodiments, energy storage module 112 may include other types of energy storage devices such as capacitors or super capacitors.

To implant LCP 100 inside a patient's body, an operator a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy. In embodiments where LCP 100 includes an accelerometer, LCP 100 may additionally be able to sense the motion of the cardiac wall to which LCP 100 is attached.

Figure 2:
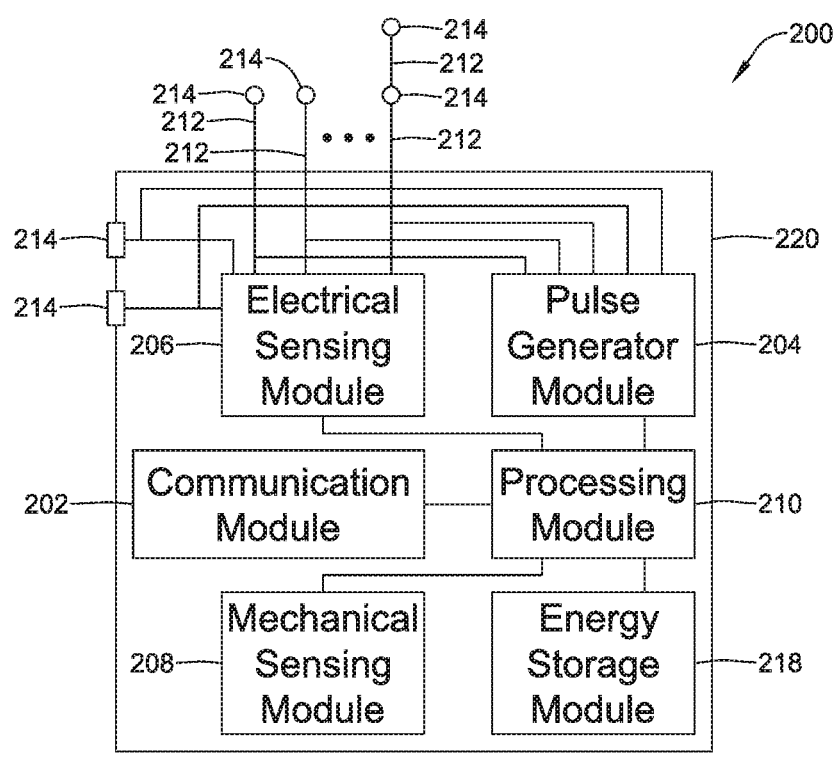
FIG. 2 is a schematic block diagram of another illustrative medical device that may be used in conjunction with the LCP of FIG. 1.

FIG. 2 depicts an embodiment of another device, medical device (MD) 200, which may operate to sense physiological signals and parameters and deliver one or more types of electrical stimulation therapy to tissues of the patient. In the embodiment shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to and/or different than modules 102, 104, 106, 108, and 110 of LCP 100 in one or more manners. Additionally, energy storage module 218 may be similar to and/or different than energy storage module 112 of LCP 100 in one or more manners. However, in some embodiments, MD 200 may have a larger volume within housing 220 than a volume of LCP 100. In such embodiments, MD 200 may include a larger energy storage module 218 and/or a larger processing module 210 capable of handling more complex operations than processing module 110 of LCP 100.

While MI) 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some embodiments, leads 212 may be implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 may be positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart.

MD 200 may also include one or more electrodes 214 not disposed on a lead 212. For example, one or more electrodes 214 may be connected directly to housing 220.

The electrodes 214 may conduct intrinsically generated electrical cardiac signals to leads 212. Leads 212 may, in turn, conduct the received electrical cardiac signals to one or more of the modules 202, 204, 206, and 208 of MD 200.

In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly).

Leads 212, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, mechanical sensing module 208 may be in electrical communication with leads 212 and may receive signals generated from such sensors.

While not required, in some embodiments MI) 200 may be an implantable medical device. In such embodiments, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such embodiments, leads 212 may be implanted at one or more various locations within the patient, such as within the heart of the patient, adjacent to the heart of the patient, adjacent to the spine of the patient, or any other desired location.

In some embodiments, MD 200 may be an implantable cardiac pacemaker (ICP). In these embodiments, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some embodiments, MD 200 may additionally be configured to provide defibrillation/cardioversion therapy.

In some instances, MD 200 may be an implantable cardioverter-defibrillator (ICD). In such embodiments, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, MD 200 may be a subcutaneous implantable cardioverter-defibrillator (SICD). In embodiments where MD 200 is an SICD, one of leads 212 may be a subcutaneously implanted lead. In at least some embodiments where MD 200 is an SICD, MD 200 may include only a single lead which is implanted subcutaneously but outside of the chest cavity, however this is not required.

In some embodiments, MD 200 may not be an implantable medical device. Rather, MD 200 may be a device external to the patient's body, and electrodes 214 may be skin-electrodes that are placed on a patient's body. In such embodiments, MD 200 may be able to sense surface electrical signals (e.g. electrical cardiac signals that are generated by the heart or electrical signals generated by a device implanted within a patient's body and conducted through the body to the skin). MD 200 may further be configured to deliver various types of electrical stimulation therapy, including, for example, defibrillation therapy via skin-electrodes 214.

Figure 3:
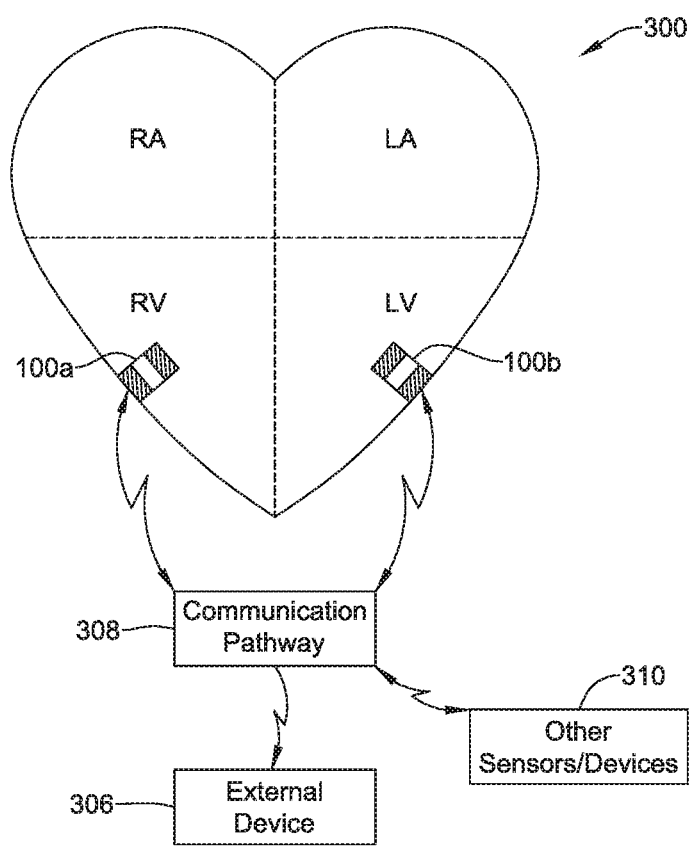
FIG. 3 is a schematic diagram of an exemplary medical system that includes multiple LCPs and/or other devices in communication with one another.

FIG. 3 illustrates an embodiment of a medical device system and a communication pathway through which multiple medical devices 100*a*, 100*b*, 306, and/or 310 of the medical device system may communicate. In the embodiment shown, medical device system 300 may include a first LCP 100*a* and a second LCP 100*b*, external medical device 306, and other sensors/devices 310.

External device 306 may be a device disposed external to a patient's body, as described previously with respect to MD 200. In at least some examples, external device 306 may represent an external support device such as a device programmer, as will be described in more detail below.

Other sensors/devices 310 may be any of the devices described previously with respect to MD 200, such as ICPs, ICDs, and SICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 100*a* and/or 100*b* may sense intrinsic cardiac electrical signals and may communicate such signals to one or more other devices 100*a*/100*b*, 306, and 310 of system 300 via communication pathway 308. In one embodiment, one or more of devices 100*a*/100*b* may receive such signals and, based on the received signals, determine an occurrence of an arrhythmia. In some cases, device or devices 100*a*/100*b* may communicate such determinations to one or more other devices 306 and 310 of system 300. In some cases, one or more of devices 100*a*/100*b*, 306, and 310 of system 300 may take action based on the communicated determination of an arrhythmia, such as by delivering a suitable electrical stimulation to the heart of the patient. One or more of devices 100*a*/100*b*, 306, and 310 of system 300 may additionally communicate command or response messages via communication pathway 308. The command messages may cause a receiving device to take a particular action whereas response messages may include requested information or a confirmation that a receiving device did, in fact, receive a communicated message or data.

It is contemplated that the various devices of system 300 may communicate via pathway 308 using RF signals, inductive coupling, optical signals, acoustic signals, or any other signals suitable for communication. Additionally, in at least some embodiments, the various devices of system 300 may communicate via pathway 308 using multiple signal types. For instance, other sensors/device 310 may communicate with external device 306 using a first signal type (e.g. RF communication) but communicate with LCPs 100*a*/100*b* using a second signal type e.g. conducted communication). Further, in some embodiments, communication between devices may be limited. For instance, as described above, in some embodiments, LCPs 100*a*/100*b* may communicate with external device 306 only through other sensors/devices 310, where LCPs 100*a*/100*b* may send signals to other sensors/devices 310, and other sensors/devices 310 relay the received signals to external device 306.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. a voltage and/or current waveform punctuated with current and/or voltage pulses, referred herein as electrical communication pulses) into the patient's body via one or more electrodes of a transmitting device, and may receive the conducted communication signals via one or more electrodes of a receiving device. The patient's body may "conduct" the conducted communication signals from the one or more electrodes of the transmitting device to the electrodes of the receiving device in the system 300. In such embodiments, the delivered conducted communication signals may differ from pacing pulses, defibrillation and/or cardioversion pulses, or other electrical stimulation therapy signals. For example, the devices of system 300 may deliver electrical communication pulses at an amplitude/pulse width that is sub-threshold. That is, the communication pulses have an amplitude/pulse width designed to not capture the heart. In some cases, the amplitude/pulse width of the delivered electrical communication pulses may be above the capture threshold of the heart, but may be delivered during a refractory period of the heart and/or may be incorporated in or modulated onto a pacing pulse, if desired.

Additionally, unlike normal electrical stimulation therapy pulses, the electrical communication pulses may be delivered in specific sequences which convey information to receiving devices. For instance, delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, a predefined sequence of communication pulses may represent a corresponding symbol (e.g. a logic "1" symbol, a logic "0" symbol, an ATP therapy trigger symbol, etc.). In some cases, conducted communication pulses may be voltage pulses, current pulses, biphasic voltage pulses, biphasic current pulses, or any other suitable electrical pulse as desired.

Figure 4:
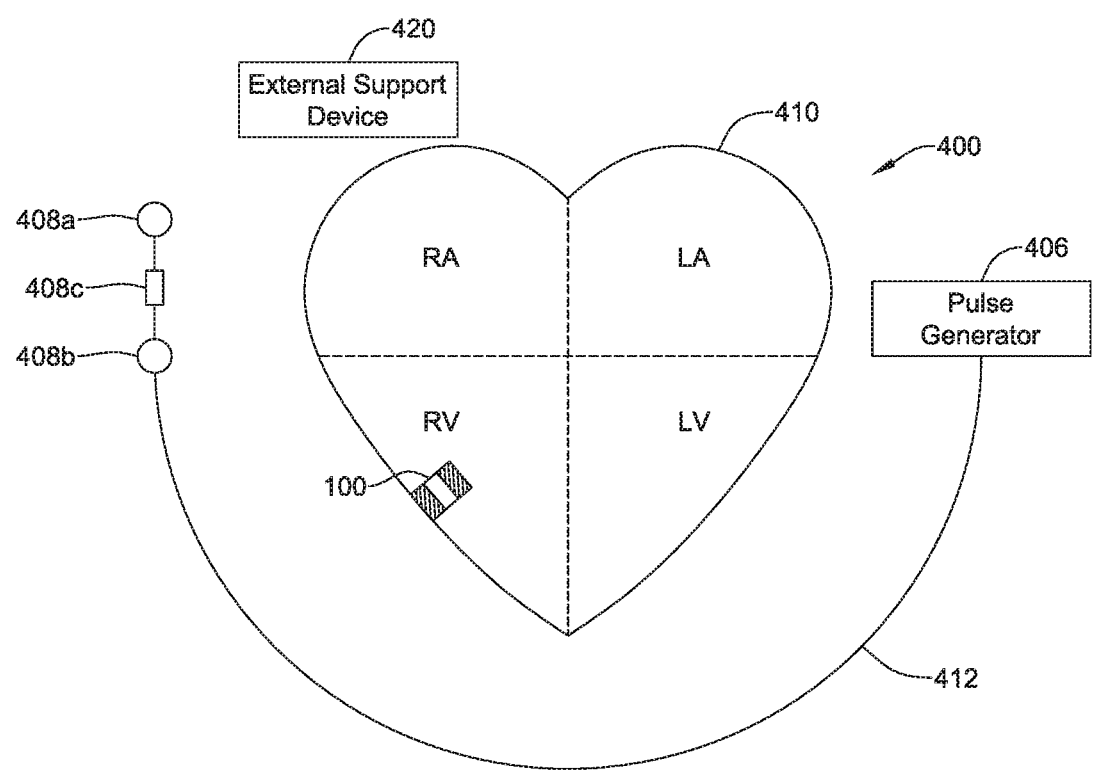
FIG. 4 is a schematic diagram of a system including an LCP and another medical device, in accordance with another embodiment of the present disclosure.

FIG. 4 depicts an illustrative medical device system 400. For example, system 400 may include multiple devices that are implanted within a patient and are configured to sense physiological signals, determine occurrences of cardiac arrhythmias, and deliver electrical stimulation to treat detected cardiac arrhythmias. In some embodiments, the devices of system 400 may be configured to determine occurrences of dislodgment of one or more devices of system 400. In FIG. 4, an LCP 100 is shown fixed to the interior of the right ventricle of the heart 410, and a pulse generator 406 is shown coupled to a lead 412 having one or more electrodes 408*a*-408*c*. In some cases, pulse generator 406 may be part of a subcutaneous implantable cardioverter-defibrillator (SICD), and the one or more electrodes 408*a*-

408c may be positioned subcutaneously adjacent the heart. LCP 100 may communicate with the SICD, such as via communication pathway 308. The locations of LCP 100, pulse generator 406, lead 412, and electrodes 408a-c depicted in FIG. 4 are just exemplary. In other embodiments of system 400, LCP 100 may be positioned in the left ventricle, right atrium, or left atrium of the heart, as desired. In still other embodiments, LCP 100 may be implanted externally adjacent to heart 410 or even remote from heart 410.

Medical device system 400 may also include external support device 420. External support device 420 can be used to perform functions such as device identification, device programming and/or transfer of real-time and/or stored data between devices using one or more of the communication techniques described herein, or other functions involving communication with one or more devices of system 400. As one example, communication between external support device 420 and pulse generator 406 can be performed via a wireless mode, and communication between pulse generator 406 and LCP 100 can be performed via a conducted communication mode. In some embodiments, communication between LCP 100 and external support device 420 is accomplished by sending communication information through pulse generator 406. However, in other embodiments, communication between the LCP 100 and external support device 420 may be via a communication module.

FIG. 4 only illustrates one example embodiment of a medical device system that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs with or without other devices such as pulse generator 406, with at least one LCP capable of delivering defibrillation therapy. Still another example may include one or more LCPs implanted along with a transvenous pacemaker and with or without an implanted SICD. In yet other embodiments, the configuration or placement of the medical devices, leads, and/or electrodes may be different from those depicted in FIG. 4. Accordingly, it should be recognized that numerous other medical device systems, different from system 400 depicted in FIG. 4, may be operated in accordance with techniques disclosed herein. As such, the embodiment shown in FIG. 4 should not be viewed as limiting in any way.

In some embodiments, LCP 100 may be configured to operate in one or more modes. Within each mode, LCP 100 may operate in a somewhat different manner. For instance, in a first mode, LCP 100 may be configured to sense certain signals and/or determine certain parameters from the sensed signals. In a second mode, LCP 100 may be configured to sense at least some different signals and/or determine at least some different parameters than in the first mode. In at least one mode, LCP 100 may be configured to determine a motion level of a patient and modulate delivery of electrical stimulation therapy based on the determined motion level of the patient. For ease of description, a mode that includes LCP 100 being configured to determine a motion level of a patient and modulate delivery of electrical stimulation therapy based on the determined motion level of the patient may be called a motion sensing mode. Other modes may include one or more programming and/or therapy modes, and it may be possible for LCP 100 to be engaged in multiple modes concurrently.

In some embodiments, LCP 100 may include a therapy mode where LCP 100 operates as a pacemaker and delivers electrical stimulation therapy, such as electrical stimulation pulses, to a heart to drive a specific heart rate for the patient. LCP 100 may be configured to modulate the rate at which LCP 100 delivers electrical stimulation therapy in order to drive different heart rates for the patient. For instance, LCP 100 may be configured to deliver electrical stimulation in a rate-adaptive manner, as described herein. In at least some of these embodiments, LCP 100 may include a motion sensing mode, which may be a specific therapy mode or may modify a therapy mode. In the motion sensing mode, LCP 100 may modulate the rate of delivery of electrical stimulation therapy based on a determined motion level of the patient.

In some cases, the LCP 100 may determine the motion level of the patient using a motion sensor (e.g. accelerometer) in the LCP 100. Determining an activity level of the patient using a motion sensor (e.g. accelerometer) in the LCP 100 can be challenging because the motion detected by the motion sensor not only includes the activity level of the patient but also the motion of the beating heart. Moreover, the motion level of the beating heart may be different for intrinsically initiated heart beats versus pace initiated heart beats.

Figure 5:
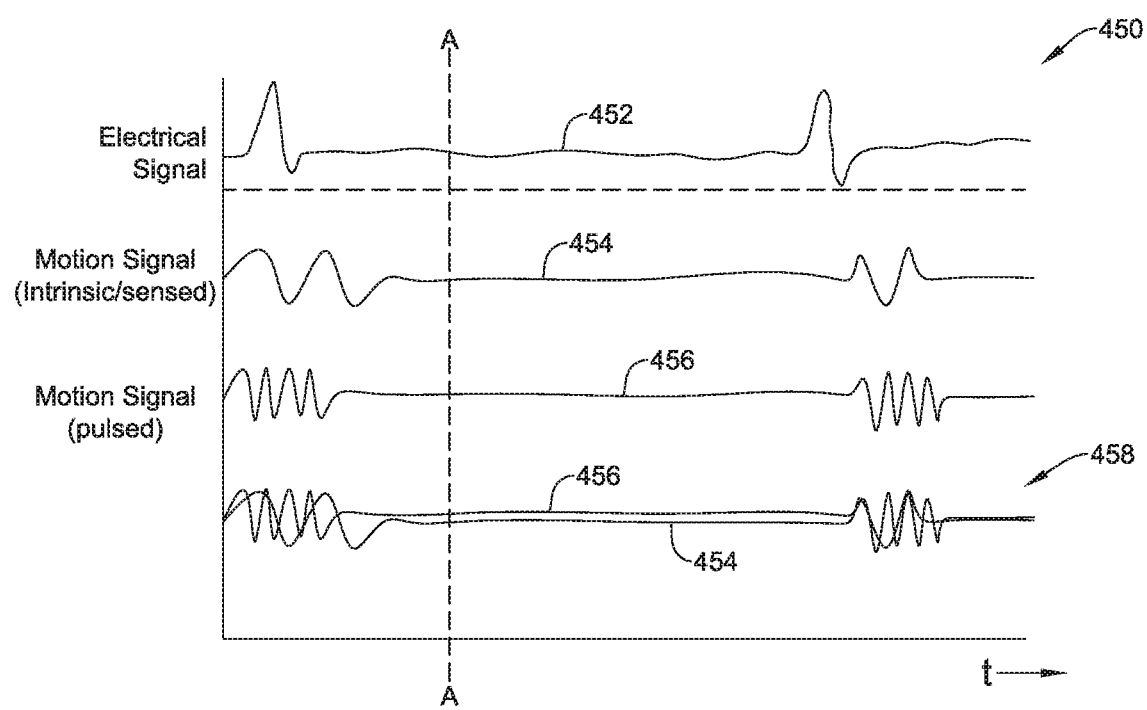
FIG. 5 depicts a graph showing a cardiac electrical signal and illustrative motion sensor signal tracings for both an intrinsically initiated heart beat and a pace initiated heart beat.

It has been found that a level of noise in a motion level of a patient (e.g. activity level) may be present when sequential heart beats switch or transition from an intrinsically initiated heart beat to a pace initiated heart and/or switches or transitions from a pace initiated heart beat to an intrinsically initiated heart beat. When adjusting a pacing therapy (e.g., an electrical stimulation therapy) based, at least in part, on a motion level of a patient (e.g. activity level), such noise may result in elevating a patient's heart rate when it is not needed and/or may result in not elevating the patient's heart rate when it is needed. Noise in motion level measurements by a motion sensor in the LCP 100 when heart beats are transitioning between an intrinsically initiated heart beat and a pace initiated heart beat are illustrated in the traces of FIG. 5. FIG. 5 depicts a graph 450 showing a number of signal traces from a motion sensor (e.g. accelerometer) of the LCP 100 when LCP 100 is attached to a wall of a patient's heart. The x-axis of graph 450 is time, t. Electrical signal 452 is an illustrative cardiac electrical signal (e.g., depicting heart beats) sensed by electrodes of the LCP 100, Motion signal 454 is an example signal sensed by an accelerometer of the mechanical sensing module 108 of the LCP 100 assuming two consecutive intrinsically initiated heart beats, Motion signal 456 is an example signal sensed by an accelerometer of the mechanical sensing module 108 of the LCP 100 assuming two consecutive pace initiated heart beats. Motion signals 454, 456 illustrate motion level measurements of the LCP 100. Tracing 458 shows the example motion signals 454 and 456 plotted to show their relative amplitudes over time. The example signal traces in FIG. 5 may be taken using an LCP 100 while the patient is in a relative static position (e.g. little or no patient activity).

Line A-A in FIG. 5 represents a time at which readings from a mechanical sensing module 108 (e.g., from a motion sensor thereof) may be taken. In some cases, a time associated with line A-A may be relative to an identified heart beat in electrical signal 452. In one example, line A-A may be set at a predetermined time after a heart beat has been detected, such as 50 milliseconds (ins), 100 ms, 150 ms, 200 ms, 250 ms, 300 ms, and/or other time period therebetween, greater than 300 ms, or less than 50 ms. In some cases, it may be desirable to consistently take measurements from the mechanical sensing module 108 during one of the systole and diastole phases of the cardiac cycle. For example, a measurement may be taken from mechanical sensing module 108 while the heart of a patient is in the systole phase (e.g., while the heart is contracting) and the acceleration of the heart may be substantially constant. It one example, taking measurements from the mechanical sensing module 108 at or at about 200 ms after a heart beat is initiated can result in a measurement during a systole phase of the cardiac cycle and while the heart is in substantial constant acceleration (e.g., constant contraction and relatively flat in FIG. 5), As can be seen from trace 458 in FIG. 5, motion signals 454 and 456 have different values at line A-A. This difference between motions signals 454 and 456 at line A-A may be considered to be a graphical representation of "noise" in the measurements taken from the mechanical sensing module 108 when sequential heart beats are not initiated by the same one of an intrinsic rhythm and a pace rhythm. The techniques herein may be utilized, individually and/or in combination, to help correct for this "noise" when determining whether to modify a pacing therapy in response to a motion level of a patient.

In rate-adaptive pacing, a motion level for an LCP 100 (e.g., an IMD) may be determined for every heart beat. Then, a motion level of a patient (e.g., an activity level) in which the LCP 100 is implanted may be identified by comparing a motion level of the LCP 100 for a current heart beat to one or more motion levels associated with one or more previous heart beats. The difference may be attributed to the activity level of the patient. However, when heart beats transition between heart beats initiated by different rhythms (e.g., an intrinsic rhythm and a pace rhythm), the aforementioned "noise" may occur resulting in larger than expected changes in motion levels of the LCP 100 that may inaccurately indicate a rise in activity level of a patient and unnecessarily raising a pacing rate of the heart.

Figure 6:
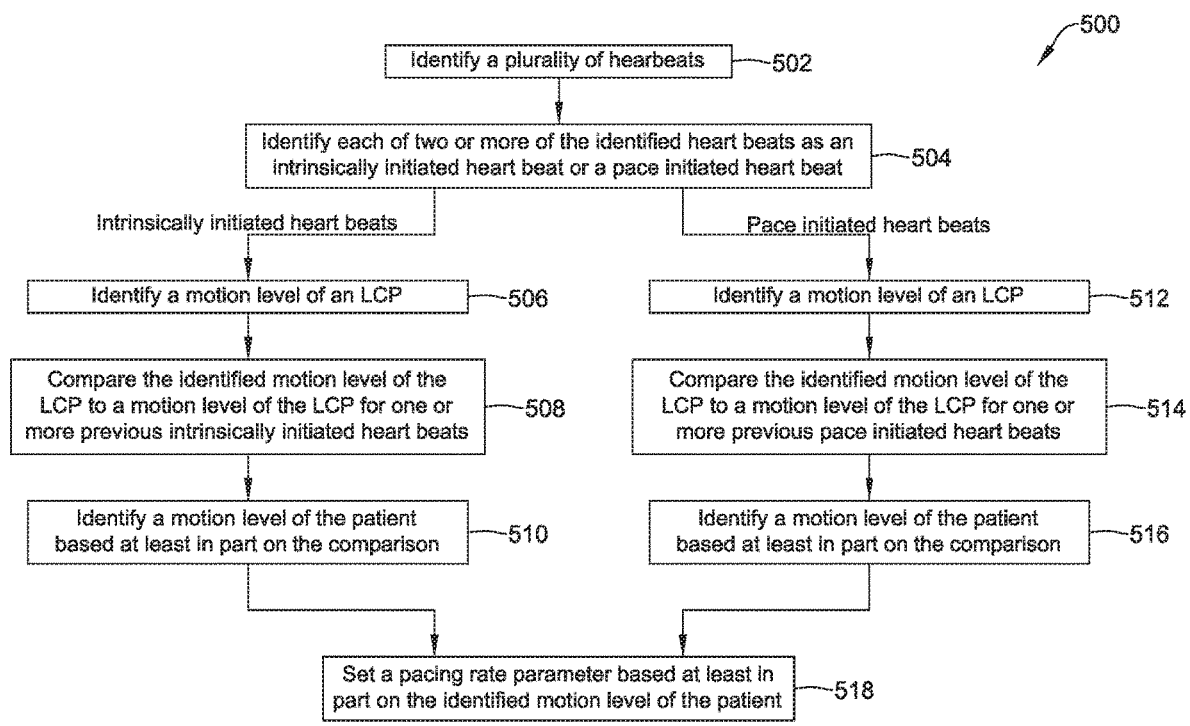
FIG. 6 depicts a schematic flow diagram of an illustrative technique for setting a pacing rate parameter for an LCP.

FIG. 6 depicts an illustrative method 500 for setting a pace rate parameter of an LCP 100 implanted in a patient's heart based, at least in part, on an identified motion level of the patient. In illustrative method 500, a plurality of heart beats may be identified 502, for example, by the electrical sensing module 106 of the implanted LCP 100. The processing module 110 of the LCP 100, or other processing module (e.g., located at or remote from the LCP), may identify 504 whether the identified heart beats were intrinsically initiated or pace initiated. The processing module 110 may distinguish intrinsically initiated heart beats, pace initiated heart beats and fusion beats by analyzing the morphology of the electrical signal 452 of the heart beat, the morphology of motion signal 454, 456, and/or using any other suitable technique. In some cases, the electrical signal 452 may be compared to an electrical signal template for an intrinsically initiated heart beat, an electrical signal template for a pace initiated heart beats and an electrical signal template for a fusion beat, and to identify which electrical signal template the electrical signal 452 most closely matches. Likewise, the motion signal may be compared to a motion signal template for an intrinsically initiated heart beat, a motion signal template for a pace initiated heart beats and a motion signal template for a fusion beat, and to identify which motion signal template the motion signal most closely matches. These are just examples.

For intrinsically initiated heart beats, the processing module 110 may identify 506 a motion level measurement from the mechanical sensing module 108 (e.g., from a motion sensor thereof) of the LCP 100 (e.g., an IMD) and compare 508 the identified motion level of the LCP 100 for a current intrinsically initiated heart beat to a motion level of the LCP 100 for one or more previous intrinsically initiated heart beats. The motion level measurement may be taken during the systole phase of the cardiac cycle, but this is not required. Based, at least in part on the comparison, the processing module 110, or other processing module, may identify 510 a motion level of the patient in which the LCP 100 is implanted. Based, at least in part on the identified motion level of the patient, the processing module 110, or other processing module, may set 518 a pacing rate parameter for the LCP 100.

For pace initiated heart beats, the processing module 110 may identify 512 a motion level measurement from the mechanical sensing module 108 for the LCP 100 (e.g., an IMD and compare 514 the identified motion level of the LCP 100 for a current pace initiated heart beat to a motion level of the LCP 100 for one or more previous pace initiated heart beats. Based, at least in part on the comparison, the processing module 110, or other processing module, may identify 516 a motion level of the patient in which the LCP 100 is implanted. Based, at least in part on the identified motion level of the patient, the processing module 110, or other processing module, may set 518 a pacing rate parameter for the LCP 100.

In some cases, and as discussed above with respect to rate-adaptive pacing, comparing the identified motion level of the LCP 100 for a current heart beat to a motion level of the LCP 100 for a previous heart beat may include determining a difference between the compared motion levels. Then, based on this difference, the processing module 110 of the LCP 100 may set or update the motion level of the patient (e.g. activity level) and thus, set or update a pacing rate parameter for the LCP 100. In one example, the value of the motion level of the patient may be an absolute value of the difference between the motion level corresponding to a current heart beat and the motion level corresponding to the previous heart beat, but other relationships are contemplated. This general process, along with others, for comparing motion levels of the LCP 100 associated with different heart beats and determining a motion level of a patient may be utilized in the various techniques discussed herein.

Alternatively, or in addition to, comparing 508, 514 a motion level of an LCP 100 (e.g., an IMD) for a current heart beat to a motion level of the LCP 100 for an immediately previous heart beat, the processing module 110 may compare the motion level of an LCP 100 for a current heart beat to an average of motion levels of the LCP 100 for N previous heart beats (e.g., two or more previous heart beats) that were initiated by a same rhythm (e.g., intrinsic rhythm or pace rhythm) as is the current heart beat. The average of motion levels of the LCP 100 for N previous heart beats may be a straight average, a weighted average (e.g., where motion levels associated with one or more previous heart beats is weighted greater than another motion level associated with a heart beat), and/or one or more other average of motion levels. In other instances, the motion level of the LCP 100 may be compared to one or more other statistical analyses related to motion levels of the LCP 100 associated with previous heart beats. The comparison may then be used to determine a motion level of a patient and/or used to set a pacing rate for the LCP 100.

The number of N previous heart beats may be determined by a sliding or moving time window that extends back a predetermined amount of time or a predetermined number of beats from a current heart beat. In one example, there may be a predetermined amount of time, t, before the current heart beat and seven (7) heart beats occur during the time t.

Of these seven heart beats, four may be intrinsically initiated heart beats and three may be pace initiated heart beats. Thus, if the current heart beat is an intrinsically initiated heart beat, a motion level associated with the current heart beat may be compared to an average of the four motion levels associated with the four intrinsically initiated heart beats within time t. If the current heart beat is a pace initiated heart beat, a motion level associated with the current heart beat may be compared to an average of the three motion levels associated with the three pace initiated heart beats within time t. A predetermined time t may be any time less than one (1) second, a time between one (1) second and three (3) minutes, a time between one (1) second and two (2) minute, one (1) second and one (1) minute, or any time greater than three (3) minutes.

If no heart beats occurring within the sliding or moving window were initiated by a same rhythm type (e.g., intrinsic or pace) as the current heart beat, then a motion level of the LCP 100 associated with the current heart beat may not be compared to a motion level associated with a heart beat or one or more other actions may be taken. In such instances, a motion level of a patient may not be updated and a pace rate for the LCP 100 may not be updated or re-set in response to the current heart beat.

Although the sliding or moving window is discussed with respect to averaging motion levels associated with previous heart beats initiated in the same manner as a current heart beat, the sliding or moving window may be utilized in other circumstances and/or without averaging motion levels within the window. For example, the processing module 110 may compare a motion level of the LCP 100 to a motion level of the LCP 100 associated with one previous and similarly initiated heart beat within the sliding or moving window. That is, all motion levels associated with previous similarly initiated heart beats outside of the sliding or moving window may be dropped and a motion level associated with a current heart beat may be compared to a motion level associated with the most recent similarly initiated heart beat within the window. Additionally or alternatively, if there are no previous similarly initiated heart beats within the sliding or moving window, a second or further sliding or moving window (e.g., having a longer duration than the first sliding or moving window) may be utilized. In such cases, an average of the motion levels associated with the previous similarly initiated heart beats in the second or further sliding or moving window may be compared to the motion level of the current heart, but this is not required.

In some cases, the LCP 100 may skip setting a pacing rate based, at least in part, on a motion level of the patient associated with a most recent heart beat and instead, maintain the previously established pacing rate for the most recent heart beat. For example, if a most recent heart beat is identified as an intrinsically initiated heart beat or a pace initiated heart beat and is directly after (e.g., immediately after or sequentially follows) a heart beat initiated by the same type of rhythm, then the LCP 100 may set a pacing rate based, at least in part, on a motion level of the patient associated with the most recent heart beat, as discussed with respect to illustrative method 500. However, in the example, if a most recent heart beat is initiated by a different type of rhythm than an immediately previous heart beat, the LCP 100 may maintain the pace rate previously established, and essentially ignore the most recent heart beat.

Figure 7:
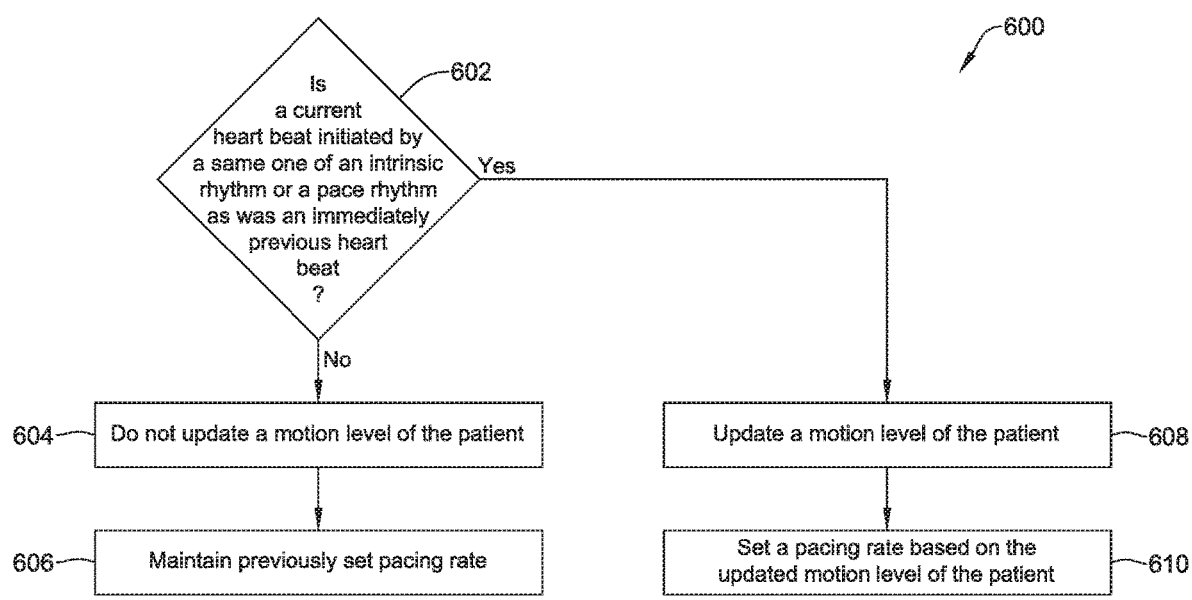
FIG. 7 depicts a schematic flow diagram of an illustrative technique for setting a pacing rate parameter for an LCP.

FIG. 7 depicts an illustrative method 600 for determining whether to update a motion level of a patient (e.g. activity level) based on a current heart beat and thus, update the set pacing rate. Illustrative method 600 may be carried out by the processing module 110 of the LCP and may be used individually or in combination with the other techniques and processes described herein.

As shown in FIG. 7, illustrative method 600 may include determining 602 whether a currently identified heart beat is initiated by a same one of an intrinsic rhythm or a pace rhythm as was an immediately previous heart beat. If the currently identified heart beat is not initiated by a same one of an intrinsic rhythm or a pace rhythm as was an immediately previous heart beat, then the LCP 100 may skip updating 604 a motion level of the patient for the current heart beat. In some cases, not updating 604 a motion level of the patient may include either not identifying a motion level of the LCP 100 for a current heart beat or ignoring an identified motion level of the LCP 100 for the current heart beat. As a result, a previously set pacing rate for the patient may be maintained 606. In some cases, instead of maintaining 606 a previously set pacing rate for the patient, the processing module 110 may take one or more steps to change the pacing rate based on one or more parameters other than a motion level of the patient.

In illustrative method 600, if the currently identified heart beat is initiated by a same one of an intrinsic rhythm or a pace rhythm as was an immediately previous heart beat, then the LCP 100 may update 608 a motion level of the patient. In one example, a motion level of a patient may be updated by the processing module 110 or other processing module by identifying a motion level of the LCP 100 from the mechanical sensing module 108 (e.g. from accelerometer signal), comparing the identified motion level of the LCP 100 to a motion level of the LCP 100 for the immediately previous heart beat and determining a motion level of the patient based, at least in part, on the comparison, but this is not required and other techniques may be utilized. Once the motion level of the patient has been updated, the LCP 100 may update (e.g., set) 610 a pacing rate based, at least in part, on the updated motion level of the patient.

In some instances, a fusion initiated heart beat may occur. A fusion initiated heart beat is a heart beat in which a pace rhythm and an intrinsic rhythm of the heart occur at the same or close to the same time and cause a fusion heart beat. If a currently identified heart beat is a fusion initiated heart beat, then the LCP 100 may skip updating a motion level of a patient for the current heart beat. In some cases, not updating or identifying a motion level of the patient may include either not identifying a motion level of the LCP 100 for the current heart beat or ignoring an identified motion level of the LCP 100 for the current heart beat. As a result, a previously set pacing rate for the patient may be maintained. In some cases, instead of maintaining a previously set pacing rate for the patient, the processing module 110 may take one or more steps to change the pace rate based on one or more parameters other than a motion level of the patient.

Figure 8:
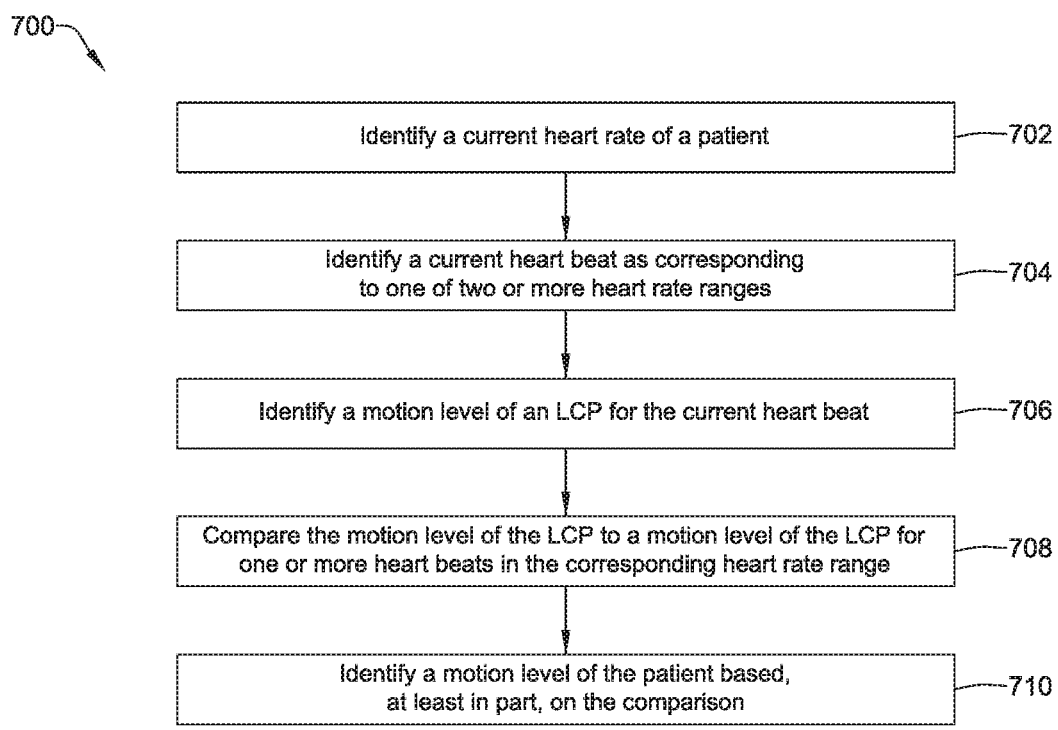
FIG. 8 depicts a schematic flow diagram of an illustrative technique for setting a pacing rate parameter for an LCP utilizing heart rate range classifications.

FIG. 8 depicts an illustrative method 700 that may be effected by the processing module 110 of the LCP 100 and may be used individually or in combination with the other techniques and processes described herein. In illustrative method 700, a current heart rate of a patient may be identified 702 and based, at least in part, on the identified heart rate, a current heart beat may be identified 704 as corresponding to a particular heart rate range of two or more heart rate ranges. The heart rate ranges may be determined in any manner. In one example, a first heart rate range may be indicative of a resting activity level for a patient, a second heart rate range may be indicative of an active activity level for the patient (e.g. walking), and a third heart rate range may be indicative of a strenuous activity level of the patient (e.g. running). Additionally, in some cases, the heart beats identified as corresponding to each heart rate range may be further classified as being either intrinsically or pace initiated. For a current heart beat intrinsically initiated or pace initiated, a motion level of an LCP 100 may be identified 706 and the motion level may be compared 708 to a motion level of the LCP 100 for one or more similarly initiated heart beats in the corresponding heart rate range. Then, a motion level of the patient may be identified 710 based, at least in part on the comparison.

Figure 9:
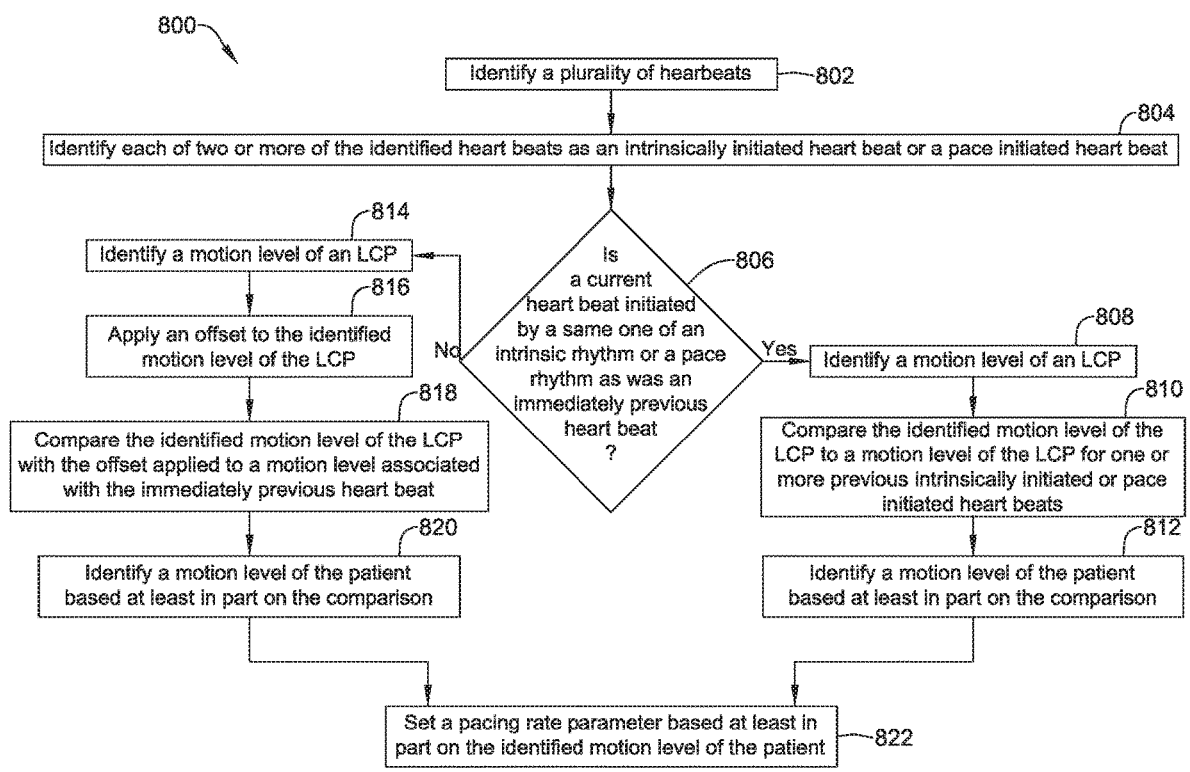
FIG. 9 depicts a schematic flow diagram of an illustrative technique for setting a pacing rate parameter for an LCP utilizing an offset.

In some cases, rather than ignoring a motion level of a current heart beat when the current heart beat is not initiated by the same intrinsic or pace rhythm, it is contemplated that an offset may be applied. The offset may be applied to correct for the "noise" in a motion level measurement taken for the current heart beat that results from the current heart beat not being initiated by the same intrinsic rhythm or pace rhythm than the immediately previous heart beat (e.g., see the offset at line A-A between motion signal 454 and motion signal 456 of FIG. 5). An illustrative method 800 is shown in FIG. 9 for using an offset for determining a motion level of a patient even for heart beats that transition from an intrinsic rhythm to a pace rhythm, and visa-versa.

The illustrative method 800 includes identifying 802 a plurality of heart beats and identifying 804 each of two or more of the identified heart beats as being an intrinsically initiated heart beat or a pace initiated heart beat. The processing module 110 of the LCP 100 may then determine 806 if a current heart beat is initiated by a same one of an intrinsic rhythm or a pace rhythm of the immediately previous heart beat. In illustrative method 800, if a current heart beat is initiated by a same one of an intrinsic rhythm or a pace rhythm of the immediately previous heart beat, the processing module 110 may identify 808 a motion level of the LCP 100 (e.g., an IMD) using a motion sensor (e.g. accelerometer) of the mechanical sensing module 108 and compare 810 the identified motion level of the LCP 100 to a motion level of the LCP 100 corresponding to one or more previous and similarly initiated (e.g., either intrinsically initiated or pace initiated) heart beats. In some cases, and similar to as discussed above, the motion level corresponding to the measurement from the motion sensor of the mechanical sensing module 108 may be taken during the systole phase of a cardiac cycle, but this is not required. Based, at least in part, on the comparison 810, the processing module 110 may identify 812 a motion level of the patient and set 822 a pacing rate parameter for the LCP 100 based, at least in part, on the identified motion level of the patient.

In illustrative method 800, if a current heart beat is initiated by a different one of an intrinsic rhythm or a pace rhythm of the immediately previous heart beat, the processing module 110 may identify 814 a motion level of the LCP 100 (e.g., an IMD) using a motion sensor (e.g. accelerometer) of the mechanical sensing module 108 and apply 816 an offset to the identified motion level. In one example, the offset may represent the offset at line A-A between motion signal 454 and motion signal 456 of FIG. 5. The identified motion level of the LCP 100 for the current heart beat with the offset applied may then be compared 818 to a motion level of the LCP 100 corresponding to the immediately previous heart beat. In some cases, and similar to that discussed above, the motion level corresponding to the measurement from the motion sensor of the mechanical sensing module 108 may be taken during the systole phase of a cardiac cycle, but this is not required. Based, at least in part, on the comparison 818, the processing module 110 may identify 820 a motion level of the patient and set a pacing rate parameter for the LCP 100 based, at least in part, on the identified motion level of the patient.

Figure 10:
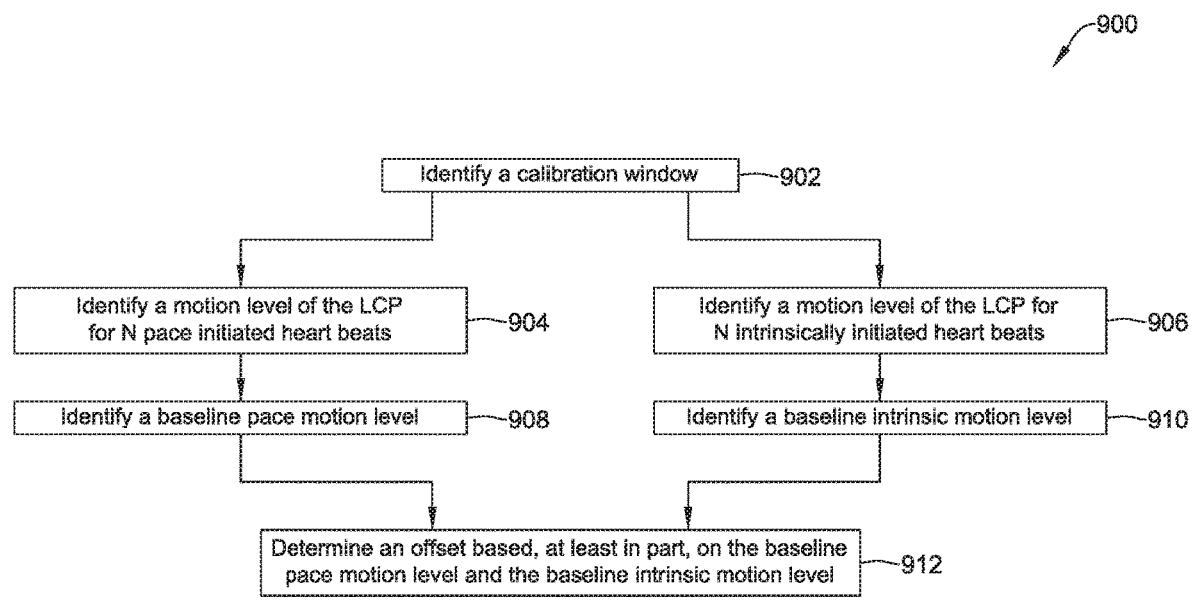
FIG. 10 depicts a schematic flow diagram of an illustrative technique for setting a pacing rate parameter for an LCP utilizing a calibration window.

One illustrative method for determine the offset is shown in FIG. 10. Illustrative method 900 of FIG. 10 may be utilized to determine the offset to be applied to a motion level of a current heart beat on a transition from a heart beat that was initiated by a different rhythm (e.g., an intrinsic rhythm or a pace rhythm). To determine the offset, the processing module 110 of the LCP 100 or other processing module may identify 902 a calibration window. In some cases, the calibration window may cover a time period or window in which N pace initiated heart beats occur and in which N intrinsically initiated heart beats occur. The illustrative method 900 may include identifying 904 a motion level of the LCP 100 (e.g., an IMD) for N pace initiated heart beats using a motion sensor of the mechanical sensing module 108 and identifying 906 a motion level of the LCP 100 for N intrinsically initiated heart beats using the motion sensor of the mechanical sensing module 108. N may be one, two, or a greater number of heart beats. The N heart beats for a particular rhythm type (e.g., intrinsic or pace) may be consecutive heart beats or may be separated by one or more heart beats initiated by the other rhythm type. In some cases, to obtain N consecutive pace initiated heart beats, it may be necessary to raise the pacing rate to a particular level above a current intrinsic heart rate (e.g., 5-30 beats per minute over the current intrinsic heart rate, 10-20 beats per minute over the current intrinsic heart rate, and/or a different level above the current intrinsic heart rate). In some cases, to obtain N consecutive intrinsically initiated heart beats, it may be necessary to lower the pacing rate to a particular level below a current intrinsic heart rate (e.g., 5-10 beats per minute below the current intrinsic heart rate and/or a different level below the current intrinsic heart rate). In some cases, the measurements taken by the motion sensor of the mechanical sensing module 108 for each of the N heart beats may be taken during the systole phase of the cardiac cycle, but this is not required.

From the identified motion levels for the N pace initiated heart beats, the processing module 110 may identify a baseline pace motion level. Similarly, from the identified motion levels for the N intrinsically initiated heart beats, the processing module 110 may identify a baseline intrinsic motion level. Based, at least in part, on the baseline pace motion level and the baseline intrinsic motion level, the processing module 110 may determine an offset that may be applied to motion levels associated with heart beats initiated by a rhythm that is different than a rhythm that initiated an immediately previous heart beat.

The baseline pace motion level and/or the baseline intrinsic motion level may be identified in any manner. In one example, the motion levels of the LCP 100 associated with the N pace initiated heart beats may be averaged to obtain the baseline pace motion level. Similarly, in an example, the motion levels of the LCP 100 associated with the N intrinsic initiated heart beats may be averaged to obtain the baseline intrinsic motion level. In addition or as an alternative to averaging of the motion levels associated with the heart beats, other analyses may be performed on the identified motion levels. For example, motion levels detected for older heart beats may be weighted less than the motion levels detected of more recently heart beats.

Figure 11A:
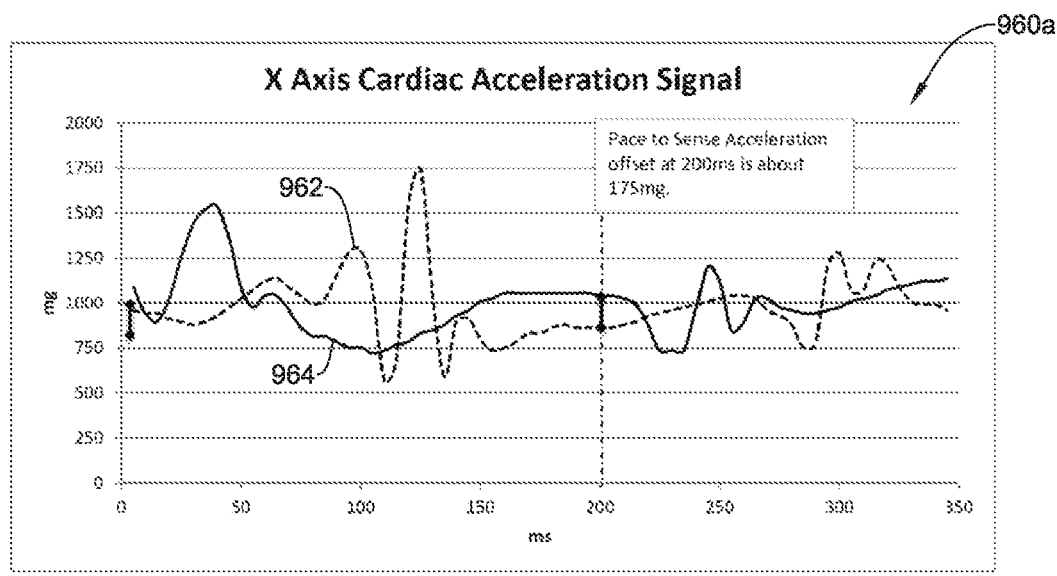
FIGS. 11A-11C depict graphs of illustrative averaged raw accelerometer data for a plurality of heart beats.
Figure 11B:
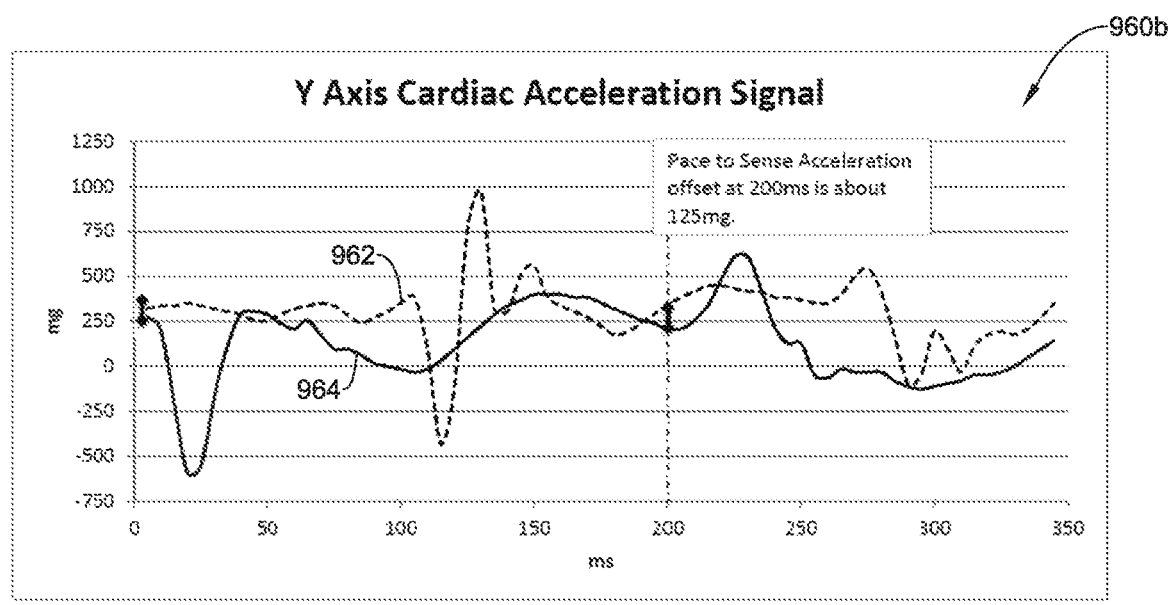
Figure 11C:
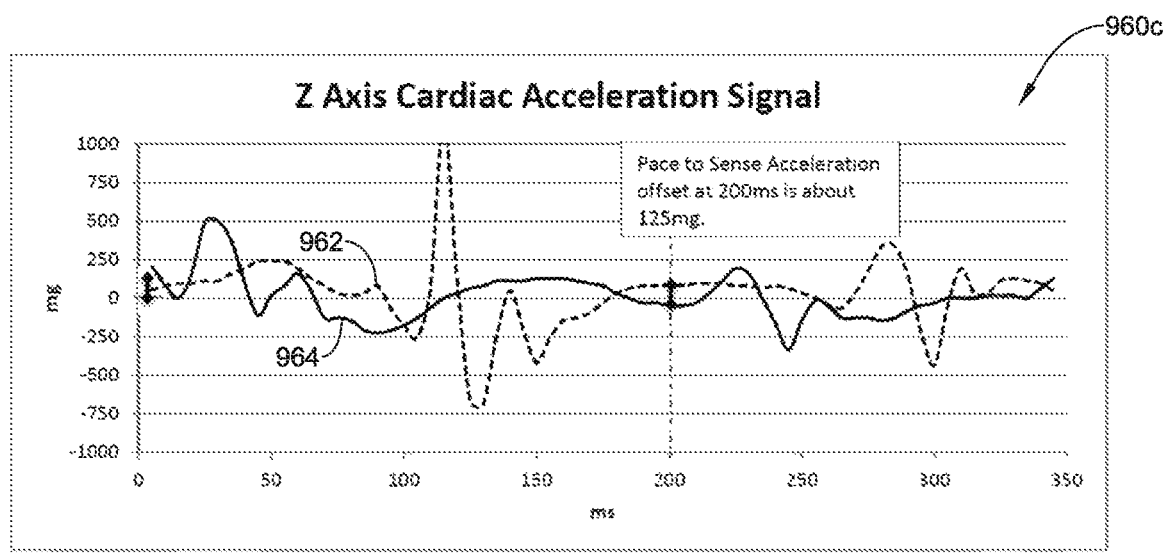

FIGS. 11A-11C show graphs 960*a*, 960*b*, 960*c*, which represent an average of motion level signals from different axes, x-axis, y-axis, and z-axis, respectively, generated by a motion sensor, such as a three-axis accelerometer, of LCP 100 for each of N pace initiated heart beats and N intrinsically initiated heart beats, where LCP 100 is attached to a wall of a patients' heart. Signal 962, shown in a dashed line in graphs 960a-960c, represents an average of accelerometer magnitude signals (e.g., a baseline motion level signal) for N pace initiated heart beats on the respective axis. Signal 964, represented in a solid line, represents an average of accelerometer magnitude signals (e.g., a baseline motion level signal) for N intrinsically initiated heart beats.

In the example depicted in FIGS. 11A-11C, an offset may be selected by determining a difference between signal 962 and 964 at a predetermined time in each graph and using the greatest difference at the predetermined time as the offset. Alternatively, the least difference at the predetermined time may be utilized as the offset. Alternatively, the difference of each axis may be averaged to determine the offset. In yet another example, one or more other analyses may be performed to determine the offset. As shown in the example of FIGS. 11A-11C, a pre-determined time may be 200 ms, at line A-A, after a heart beat has been identified. In the example, at 200 ms, the signals 962 and 964 have a difference of 175 units on the x-axis (FIG. 11A), 125 units on the y-axis (FIG. 11B), and 125 units on the z-axis (FIG. 11C). With this example, the processing module 110 or other module may select the difference of the x-axis as the offset because it is the greatest difference between signals 962 and 964 at 200 ms out from when a heart beat was initiated.

The calibration window discussed above may be identified in accordance with a predetermined time period and may begin in response to a signal from a device external to the LCP 100 or other signal. Alternatively, or in addition, a calibration window may be identified by the LCP 100 or other device after N consecutive pace initiated heart beats and/or after N consecutive intrinsically initiated heart beats, where N may be the same number or a different number of pace initiated heart beats and intrinsically initiated heart beats.

In some cases, a calibration window may be selected based on a patient activity level. In one example, a calibration window may be selected to occur while a patient in which the LCP 100 is implanted is performing no activity or is at a low activity level. Illustratively, no activity or a low activity level may include the patient sitting down, lying down, in a standing position, in a particular pose, and/or in one or more static or substantially static position.

In some cases, a calibration window may he automatically initiated to start an offset determination process (e.g., such as method 900). For example, the LCP 100 may detect when the patient is in a particular position or posture and may automatically initiate a calibration window. In some cases, the LCP 100 may detect that a motion level or activity level of the patient has crossed (e.g., fallen below or exceeded) a threshold level of motion or activity for a predetermined length of time, and then initiate a calibration window. Further, and in some cases, the LCP 100 may only automatically initiate a calibration window if it detects communication with an external device in addition to detecting that the patient is in a particular position or posture, but this is not required. Alternatively or additionally, the LCP 100 may only automatically initiate a calibration window if it detects a certain time of day. Such automatic initiation of a calibration window may allow the LCP 100 to update the offset over time to account for changing conditions.

In some cases, the LCP 100 may be configured to detect one or more positions or postures (e.g., N positions or postures) of a patient in which the LCP 100 has been implanted. This may allow the LCP 100 to: 1) create a library of offsets for different positions or postures of the patient; and 2) apply the offsets for different positions or postures when the patient is in a corresponding position or posture. For each posture or position of the patient, the processing module 110 or other processing module may identify a calibration window. During each calibration window, the processing module 110 or other processing module may identify a motion level of the LCP 100 (e.g., an IMD) using a motion sensor of the mechanical sensing module 108 for N intrinsically initiated heart beats and identify a motion level of the LCP 100 using the motion sensor for N pace initiated heart beats, where the respective N heart beats may be two or more heart beats and may or may not be consecutive heart beats. Further, measurements from the motion sensor may be taken during the systole phase of the cardiac cycle, but this is not required.

Based on the identified motion levels of the LCP 100 for the pace initiated heart beats, the processing module 110 or other processing module may identify a baseline pace motion level for the identified patient posture or position. Similarly, based on the identified motion levels of the LCP 100 for the intrinsic initiated heart beats, the processing module 110 or other processing module may identify a baseline intrinsic motion level for the identified patient posture or position. Then, in a manner similar to as discussed above with respect to method 900, the processing module may determine an offset for the identified posture or position of the patient based, at least in part, on the baseline intrinsic motion level and the baseline pace motion level for the identified posture or position.

The offsets corresponding to the various patient postures or positions may then be saved in a library in memory of the LCP 100 (e.g., memory of the processing module 110 or other memory) and/or in memory external to the LCP 100. Then, when a heart beat that is initiated by a different rhythm (e.g., intrinsic rhythm or pace rhythm) than an immediately previous rhythm is identified, the LCP 100 may identify the patient's posture or position and apply a posture or position specific offset to the motion level of an LCP 100 for the current heart beat prior to or after comparing the motion level to a motion level of the LCP 100 for the immediately previous heart beat.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. An implantable medical device (IMD) implantable within a patient's heart, the IMD comprising:
   two or more sensors including a motion sensor;
   a controller operatively coupled to the two or more sensors, the controller configured to:

identify a plurality of heart beats using one or more of the sensors, each of the plurality of heart beats having a systole phase and diastole phase;

identify each of two or more of the plurality of heart beats as an intrinsically initiated heart beat or a pace initiated heart beat;

identify a calibration time window, and during the calibration time window:

identify a baseline intrinsic motion level by identifying a motion level of the IMD using the motion sensor during N intrinsically initiated heart beats, where N is greater than two;

identify a baseline pace motion level by identifying a motion level of the IMD using the motion sensor during N pace initiated heart beats, where N is greater than two;

determine an offset based at least in part on the baseline intrinsic motion level and the baseline pace motion level;

after the calibration time window:

for an intrinsically initiated heart beat that immediately follows a pace initiated heart beat, identify a motion level of the IMD using the motion sensor and apply the offset, and compare the identified motion level of the IMD with the applied offset to a motion level of the IMD identified for the immediately preceding pace initiated heart beat, and identify a motion level of the patient based at least in part on the comparison; and set a pacing rate parameter based at least in part on the identified motion level of the patient.

2. The IMD of claim 1, wherein, after the calibration time window, the controller is further configured to:

for a pace initiated heart beat that immediately follows an intrinsic initiated heart beat, identify a motion level of the IMD using the motion sensor and apply the offset, and compare the identified motion level of the IMD with the applied offset to a motion level of the IMD identified for the immediately preceding intrinsically initiated heart beat, and identify a motion level of the patient based at least in part on the comparison.

3. The IMD of claim 2, wherein, after the calibration time window, the controller is further configured to:

for an intrinsically initiated heart beat that immediately follows an intrinsically initiated heart beat, identify a motion level of the IMD using the motion sensor during the systole phase of the intrinsically initiated heart beat, and compare the identified motion level of the IMD to a motion level of the IMD identified for one or more previous intrinsically initiated heart beats, and identify a motion level of the patient based at least in part on the comparison.

4. The IMD of claim 3, wherein, after the calibration time window, the controller is further configured to:

for a pace initiated heart beat that immediately follows a pace initiated heart beat, identify a motion level of the IMD using the motion sensor during the systole phase of the pace initiated heart beat, and compare the identified motion level of the IMD to a motion level of the IMD identified for one or more previous pace initiated heart beats, and identify the motion level of the patient based at least in part on the comparison.

5. The IMD of claim 1, wherein the N intrinsically initiated heart beats are N consecutive intrinsically initiated heart beats.

6. The IMD of claim 1, wherein the N pace initiated heart beats are N consecutive pace initiated heart beats.

7. The IMD of claim 1, wherein the calibration time window is a time window where patient activity is expected to be low.

8. The IMD of claim 1, wherein the calibration time window is initiated after a particular posture of the patient is detected by the IMD.

9. The IMD of claim 8, wherein the IMD is configured to detect each of N different postures, wherein N is greater than two, and wherein the controller is configured to:

identify a calibration time window for each N different postures, and during each calibration time window:

identify a baseline intrinsic motion level for the corresponding posture by identifying a motion level of the IMD using the motion sensor during the systole phase of N intrinsically initiated heart beats, where N is greater than two;

identify a baseline pace motion level for the corresponding posture by identifying a motion level of the IMD using the motion sensor during the systole phase of N pace initiated heart beats, where N is greater than two;

determine an offset for each of the N different postures based at least in part on the baseline intrinsic motion level that corresponds to the corresponding posture and the baseline pace motion level that corresponds to the corresponding posture;

after the calibration time window for each of the N different postures:

identify a current posture of the patient as one of the N different postures;

for an intrinsically initiated heart beat that immediately follows a pace initiated heart beat, identify a motion level of the IMD using the motion sensor during the systole phase of the intrinsically initiated heart beat and apply the offset that corresponds to the current posture, and compare the identified motion level of the IMD with the applied offset that corresponds to the current posture to a motion level of the IMD identified for the immediately preceding pace initiated heart beat, and identify a motion level of the patient based at least in part on the comparison.

10. The IMD of claim 1, wherein the calibration time window is initiated at a particular time of day.

11. The IMD of claim 1, wherein the calibration time window is initiated after the motion level of the patient falls below a threshold for at least a predetermined length of time.

12. The IMD of claim 1, wherein the controller is further configured to:

during the calibration time window:

pace the patient's heart at a pacing rate that is above a current intrinsic heart rate of the patient; and while pacing the patient's heart at the pacing rate that is above the current intrinsic heart rate of the patient, identify the baseline pace motion level by identifying the motion level of the IMD using the motion sensor during the systole phase of N pace initiated heart beats, where N is greater than two.

13. A method for identifying an activity level of a patient using a motion sensor implanted within the patient's heart, the method comprising:

identifying a plurality of heart beats using the motion sensor, each of the plurality of heart beats having a systole phase and diastole phase;

identifying each of two or more of the plurality of heart beats as an intrinsically initiated heart beat or a pace initiated heart beat;

identifying a calibration time window, and during the calibration time window:
    identifying a baseline intrinsic motion level by identifying a motion level of the IMD using the motion sensor during N intrinsically initiated heart beats, where N is greater than two;
    identifying a baseline pace motion level by identifying a motion level of the IMD using the motion sensor during N pace initiated heart beats, where N is greater than two;
determining an offset based at least in part on the baseline intrinsic motion level and the baseline pace motion level; and
after the calibration time window:
    for an intrinsically initiated heart beat that immediately follows a pace initiated heart beat, identifying a motion level of the IMD using the motion sensor and apply the offset, and comparing the identified motion level of the IMD with the applied offset to a motion level of the IMD identified for the immediately preceding pace initiated heart beat, and identifying a motion level of the patient based at least in part on the comparison.

14. The method of claim 13 further comprising setting a pacing rate parameter based at least in part on the identified motion level of the patient.

15. The method of claim 13, wherein, after the calibration time window, the method further comprises:
    for a pace initiated heart beat that immediately follows an intrinsic initiated heart beat, identifying a motion level of the IMD using the motion sensor and apply the offset, and comparing the identified motion level of the IMD with the applied offset to a motion level of the IMD identified for the immediately preceding intrinsically initiated heart beat, and identifying a motion level of the patient based at least in part on the comparison.

16. The method of claim 13, wherein, after the calibration time window, the method further comprises:
    for an intrinsically initiated heart beat that immediately follows an intrinsically initiated heart beat, identifying a motion level of the IMD using the motion sensor during the systole phase of the intrinsically initiated heart beat, and comparing the identified motion level of the IMD to a motion level of the IMD identified for one or more previous intrinsically initiated heart beats, and identifying a motion level of the patient based at least in part on the comparison; and
    for a pace initiated heart beat that immediately follows a pace initiated heart beat, identifying a motion level of the IMD using the motion sensor during the systole phase of the pace initiated heart beat, and comparing the identified motion level of the IMD to a motion level of the IMD identified for one or more previous pace initiated heart beats, and identifying the motion level of the patient based at least in part on the comparison.

17. The method of claim 13, wherein the N intrinsically initiated heart beats are N consecutive intrinsically initiated heart beats, and wherein the N pace initiated heart beats are N consecutive pace initiated heart beats.

18. A leadless cardiac pacemaker (LCP) implantable within a patient's heart, the LCP comprising:
    a housing;
    two or more electrodes secured relative to the housing, the two or more electrodes are configured to sense electrical signals of the patient's heart;
    an accelerometer situated inside of the housing;
    circuitry situated inside of the housing and operatively coupled to the two or more electrodes and the accelerometer, the circuitry is configured to:
        identify a plurality of heart beats using two or more of the electrodes, each of the plurality of heart beats having a systole phase and diastole phase;
        identify each of two or more of the plurality of heart beats as an intrinsically initiated heart beat or a pace initiated heart beat;
        identify a calibration time window, and during the calibration time window:
            identify a baseline intrinsic motion level by identifying a motion level of the LCP using the accelerometer during the systole phase of N intrinsically initiated heart beats, where N is greater than two;
            identify a baseline pace motion level by identifying a motion level of the LCP using the accelerometer during the systole phase of N pace initiated heart beats, where N is greater than two;
        identify an offset based at least in part on the baseline intrinsic motion level and the baseline pace motion level;
        after the calibration time window:
            for an intrinsically initiated heart beat that immediately follows a pace initiated heart beat, identify a motion level of the LCP using the accelerometer during the systole phase of the intrinsically initiated heart beat and apply the offset, and compare the identified motion level of the LCP with the applied offset to a motion level of the LCP identified for the immediately preceding pace initiated heart beat, and identify a motion level of the patient based at least in part on the comparison;
            for a pace initiated heart beat that immediately follows an intrinsic initiated heart beat, identify a motion level of the LCP using the accelerometer during the systole phase of the pace initiated heart beat and apply the offset, and compare the identified motion level of the LCP with the applied offset to a motion level of the LCP identified for the immediately preceding intrinsically initiated heart beat, and identify a motion level of the patient based at least in part on the comparison;
            for an intrinsically initiated heart beat that immediately follows an intrinsically initiated heart beat, identify a motion level of the LCP using the accelerometer during the systole phase of the intrinsically initiated heart beat, and compare the identified motion level of the LCP to a motion level of the LCP identified for one or more previous intrinsically initiated heart beats, and identify a motion level of the patient based at least in part on the comparison;
            for a pace initiated heart beat that immediately follows a pace initiated heart beat, identify a motion level of the LCP using the accelerometer during the systole phase of the pace initiated heart beat, and compare the identified motion level of the LCP to a motion level of the LCP identified for one or more previous pace initiated heart beats, and identify the motion level of the patient based at least in part on the comparison; and
        set a pacing rate parameter based at least in part on the identified motion level of the patient.

19. The LCP of claim 18, wherein the N intrinsically initiated heart beats are N consecutive intrinsically initiated heart beats, and wherein the N pace initiated heart beats are N consecutive pace initiated heart beats.

20. The LCP of claim 18, wherein the calibration time window is a time window where patient activity is expected to be low.

* * * * *